(12) United States Patent
Heer et al.

(10) Patent No.: US 8,093,249 B2
(45) Date of Patent: Jan. 10, 2012

(54) PYRAZOLO[1,5-A]PYRIMIDINE-CARBONYL-PIPERAZINE DERIVATIVES

(75) Inventors: Jag Paul Heer, Harlow (GB); David Norton, Harlow (GB); Simon E Ward, Harlow (GB)

(73) Assignee: Convergence Pharmaceuticals Limited, London (GB)

( * ) Notice: Subject to any disclaimer, the term of this patent is extended or adjusted under 35 U.S.C. 154(b) by 247 days.

(21) Appl. No.: 12/503,135

(22) Filed: Jul. 15, 2009

(65) Prior Publication Data

US 2010/0016330 A1 Jan. 21, 2010

(30) Foreign Application Priority Data

Jul. 17, 2008 (GB) .................................. 0813144.3

(51) Int. Cl.
*A61K 31/497* (2006.01)
*C07D 487/00* (2006.01)
(52) U.S. Cl. .................... 514/252.16; 544/281
(58) Field of Classification Search .................... None
See application file for complete search history.

(56) References Cited

U.S. PATENT DOCUMENTS

| | | | |
|---|---|---|---|
| 5,112,824 | A | 5/1992 | Baldwin et al. |
| 2002/0115854 | A1 | 8/2002 | Lam et al. |
| 2005/0153981 | A1 | 7/2005 | Li et al. |
| 2007/0142394 | A1 | 6/2007 | Solomon et al. |
| 2008/0188484 | A1 | 8/2008 | Nettekoven et al. |
| 2008/0188487 | A1 | 8/2008 | Nettekoven et al. |

FOREIGN PATENT DOCUMENTS

| | | |
|---|---|---|
| DE | 102004054053 A1 | 5/2006 |
| EP | 1314733 A1 | 11/2001 |
| WO | 9504062 A1 | 2/1995 |
| WO | 9630343 A1 | 10/1996 |
| WO | 9631501 A1 | 10/1996 |
| WO | 9728139 A1 | 8/1997 |
| WO | 9817625 A1 | 4/1998 |
| WO | 9906371 A1 | 2/1999 |
| WO | 9937304 A1 | 7/1999 |
| WO | 0012074 A3 | 3/2000 |
| WO | 0042011 A1 | 7/2000 |
| WO | 0164676 A3 | 9/2001 |
| WO | 0166534 A2 | 9/2001 |
| WO | 0176693 A1 | 10/2001 |
| WO | 02088115 A1 | 11/2002 |
| WO | 03048139 A1 | 6/2003 |
| WO | 03062212 A1 | 7/2003 |
| WO | 03076422 A1 | 9/2003 |
| WO | 03087086 A3 | 10/2003 |
| WO | 03088967 A1 | 10/2003 |
| WO | 2005044797 A1 | 5/2005 |
| WO | 2005089502 A3 | 9/2005 |
| WO | 2005095362 A1 | 10/2005 |
| WO | 2005113542 A3 | 12/2005 |
| WO | 2006034341 A3 | 3/2006 |
| WO | 2006040181 A2 | 4/2006 |
| WO | 2006048209 A1 | 5/2006 |
| WO | 2006129122 A1 | 12/2006 |
| WO | 2007070760 A3 | 6/2007 |
| WO | 2007075524 A2 | 7/2007 |
| WO | 2007087068 A3 | 8/2007 |
| WO | 2007110449 A1 | 10/2007 |
| WO | 2007118853 A1 | 10/2007 |
| WO | 2008008398 A2 | 1/2008 |
| WO | 2008023720 A1 | 2/2008 |
| WO | 2008024284 A3 | 2/2008 |
| WO | 2008048914 A1 | 4/2008 |
| WO | 2008075019 A1 | 6/2008 |
| WO | 2008124118 A1 | 10/2008 |
| WO | 2008150470 A1 | 12/2008 |
| WO | 2008150477 A1 | 12/2008 |
| WO | 2009040659 A2 | 4/2009 |
| WO | 2009045382 A1 | 4/2009 |
| ZA | 9710062 | 5/1998 |

OTHER PUBLICATIONS

Zamponi et al., *Role of Voltage-Gated Calcium Channels in Ascending Pain Pathways*, Brain Res Rev. Apr. 2009; 60(1), pp. 84-89.
Heinke et al., *Pre- and Postsynaptic Contributions of Voltage-Dependant $Ca^{2+}$ Channels to Nociceptive Transmission in Rat Spinal Lamina L Neurons*, 2004, European Journal of Neuroscience, vol. 19, pp. 103-111.
Matthews et al., *Effects of Spinally Delivered N-and P-Type Voltage-Dependent Calcium Channel Antagonists on Dorsal Horn Neuronal Responses in a Rat Model of Neuropathy*, Department of Pharmacology, University College London, 2001 International Association for the Study of Pain, Pain 92 (2001), pp. 235-246.

*Primary Examiner* — James O Wilson
*Assistant Examiner* — Jeffrey Murray
(74) *Attorney, Agent, or Firm* — Womble Carlyle Sandridge & Rice, LLP

(57) ABSTRACT

The present invention relates to novel piperazine derivatives; to processes for their preparation; to pharmaceutical compositions containing the derivatives; and to the use of the derivatives in therapy to treat diseases for which blocking the $Ca_v2.2$ calcium channels is beneficial.

23 Claims, No Drawings

PYRAZOLO[1,5-A]PYRIMIDINE-CARBONYL-PIPERAZINE DERIVATIVES

This application claims priority to GB Application No. 0813144.3 filed Jul. 17, 2008 in the United Kingdom, the disclosure of which is incorporate herein by reference in its entirety.

The present invention relates to novel piperazine derivatives; to processes for their preparation; to pharmaceutical compositions containing the derivatives; and to the use of the derivatives in therapy to treat diseases for which blocking the $Ca_v2.2$ calcium channels is beneficial.

Pre-synaptic $Ca_v2.2$ (N-type) voltage-gated calcium channels in the dorsal horn of the spinal cord modulate the release of key pro-nociceptive neurotransmitters such as glutamate, substance P (SP) and calcitonin-gene-related peptide (CGRP), indicating the potential therapeutic use of $Ca_v2.2$ calcium channel blockers as analgesics.

Peptidic ω-conotoxins, isolated from the venom of cone snails, have been shown to be selective for $Ca_v2.2$ calcium channels and can block SP release in the spinal cord (Smith et al. (2002) Pain, 96: 119-127). Moreover, they have been shown to be antinociceptive in animal models of chronic pain following intrathecal administration (Bowersox et al. (1996) Journal of Pharmacology and Experimental Therapeutics, 279: 1243-1249; Smith et al. (2002) supra), and have been shown to be effective analgesics in clinical use, particularly in the treatment of neuropathic pain (Brose et al. (1997) Clinical Journal of Pain, 13: 256-259).

In addition, $Ca_v2.2$ calcium channels have been shown to be important for normal neuronal function (Winquist et al. (2005) Biochemical Pharmacology, 70: 489-499). Therefore, the aim is to identify novel molecules that preferentially block $Ca_v2.2$ under conditions of increased neuronal excitability, so-called use-dependent blockers, as is the case in chronic pain syndromes.

WO 2007/111921 (Amgen Inc) describes a series of diazaheterocyclic amide derivatives which are claimed to be useful in the treatment of diabetes, obesity and related conditions and disorders. WO 2008/024284 (Merck & Co) describes a series of sulfonylated piperazines as cannabinoid-1 (CB1) receptor modulators which are claimed to be useful in the treatment for example of psychosis, cognitive disorders and Alzheimer's disease.

The present invention provides compounds which are capable of blocking these $Ca_v2.2$ calcium channels.

In a first aspect, there is provided a compound of formula (I), or a salt thereof, wherein:

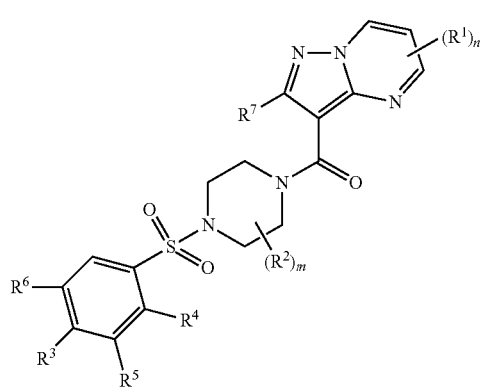

(I)

$R^1$ is $C_{1-4}$ alkyl, halogen or cyano;
m and n are selected from 0, 1 and 2;
$R^2$ is $C_{1-4}$ alkyl;
$R^3$ is hydrogen, cyano, $C_{1-4}$ haloalkyl, $C_{1-4}$ haloalkoxy or halogen;
$R^4$ is hydrogen or $C_{1-4}$ alkyl;
$R^5$ is hydrogen, cyano, $C_{1-4}$ haloalkyl, $C_{1-4}$ haloalkoxy or halogen;
$R^6$ is hydrogen, cyano, $C_{1-4}$ haloalkyl, $C_{1-4}$ haloalkoxy or halogen;
such that at least 1 of $R^3$, $R^4$, $R^5$ and $R^6$ is a group other than hydrogen;
$R^7$ is hydrogen or $C_{1-4}$ alkyl; such that when $R^7$ is $C_{1-4}$ alkyl, n is 0.

It is understood that in formula (I), when present, $R^1$ may be attached to any one of the three possible carbon atoms in the 6 membered ring.

As used herein, the term "alkyl" (when used as a group or as part of a group) refers to a straight or branched hydrocarbon chain containing the specified number of carbon atoms. For example, $C_{1-4}$ alkyl means a straight or branched hydrocarbon chain containing at least 1 and at most 4 carbon atoms. Compounds of alkyl include, but are not limited to; methyl (Me), ethyl (Et), n-propyl, i-propyl, t-butyl, n-butyl and i-butyl.

As used herein, the term "alkoxy" (when used as a group or as part of a group) refers to an —O-alkyl group wherein alkyl is as defined hereinbefore.

The term 'halogen' is used herein to describe, unless otherwise stated, a group selected from fluoro (fluorine), chloro (chlorine), bromo (bromine) or iodo (iodine).

The term $C_{1-4}$ haloalkyl as used herein refers to a $C_{1-4}$ alkyl group as defined herein substituted with one or more halogen groups, e.g. $CF_3$, $CF_2H$ or $CF_3CH_2$.

The term $C_{1-4}$ haloalkoxy as used herein refers to an $C_{1-4}$ alkoxy group as defined herein substituted with one or more halogen groups, e.g. —O—$CF_3$.

In one embodiment of the first aspect, n is 0 or 1. In a particular embodiment of the first aspect, n is 0.

In one embodiment of the first aspect, when present, $R^1$ is selected from methyl, fluoro, chloro and cyano. In a particular embodiment of the first aspect, $R^1$ is selected from methyl and fluoro. In a more particular embodiment of the first aspect, $R^1$ is selected from methyl.

In one embodiment of the first aspect, $R^7$ is selected from hydrogen and methyl. In a particular embodiment of the first aspect, $R^7$ is hydrogen.

In one embodiment of the first aspect, when present, $R^2$ is methyl. In a particular embodiment of the first aspect, $R^2$ is methyl and m is 1. In a more particular embodiment of the first aspect, the compound of formula (I) is a compound of formula (Ia)

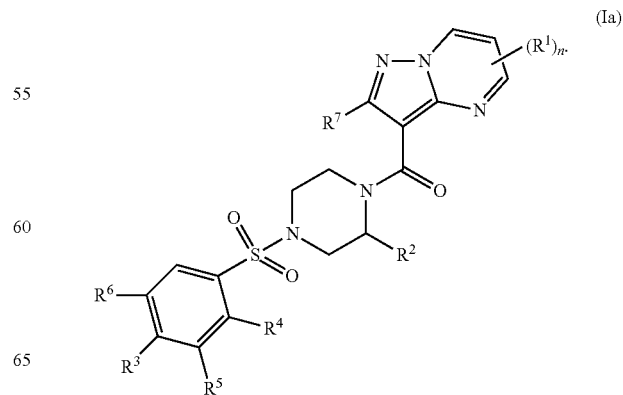

(Ia)

In an even more particular embodiment of the first or second aspect, the compound of formula (I) is a compound of formula (Ib)

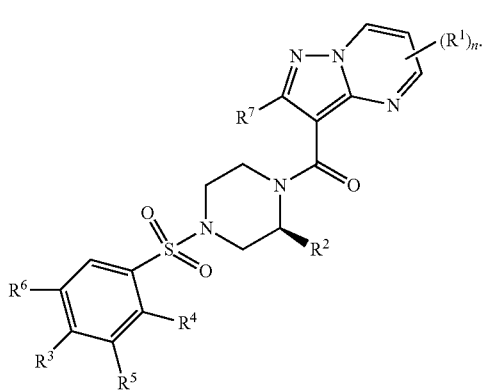

In one embodiment of the first aspect, $R^3$ is selected from trifluoromethyl, cyano, trifluoromethoxy and hydrogen. In a particular embodiment of the first aspect, $R^3$ is selected from trifluoromethyl and trifluoromethoxy. In a more particular embodiment of the first aspect, $R^3$ is trifluoromethyl.

In a particular embodiment of the first aspect, $R^4$ is hydrogen or methyl. In a more particular embodiment of the first aspect, $R^4$ is hydrogen.

In a particular embodiment of the first aspect, $R^5$ and $R^6$ are independently selected from hydrogen and $C_{1-4}$ haloalkyl. In a particular embodiment of the first aspect, $R^5$ and $R^6$ are independently selected from hydrogen and trifluoromethyl. In a more particular embodiment of the first aspect, $R^5$ and $R^6$ are hydrogen.

In one embodiment of the first aspect, n is 0 or 1; when present, $R^1$ is selected from methyl, fluoro, chloro and cyano; $R^7$ is selected from hydrogen and methyl; when present, $R^2$ is methyl; $R^3$ is selected from trifluoromethyl, cyano, trifluoromethoxy and hydrogen; $R^4$ is hydrogen or methyl; and $R^5$ and $R^6$ are independently selected from hydrogen and $C_{1-4}$ haloalkyl.

In one embodiment of the first aspect, n is 0; $R^7$ is hydrogen; $R^2$ is methyl and m is 1; $R^3$ is selected from trifluoromethyl and trifluoromethoxy; $R^4$ is hydrogen; and $R^5$ and $R^6$ are independently selected from hydrogen and trifluoromethyl.

In one embodiment of the first aspect, n is 0; $R^7$ is hydrogen; $R^2$ is 2-methyl in relation to the piperazine carbonyl bond (as in formula (Ia)) and m is 1; $R^3$ is selected from trifluoromethyl and trifluoromethoxy; $R^4$ is hydrogen; and $R^5$ and $R^6$ are hydrogen.

In a second aspect, the compound of formula (I) is a compound of formula (Ic), or a salt thereof, wherein:

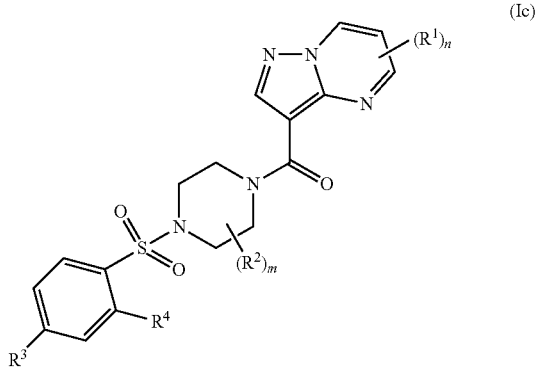

$R^1$ represents $C_{1-4}$ alkyl;
n represents an integer from 0 or 1;
m represents an integer from 0 to 1;
$R^2$ represents $C_{1-4}$ alkyl;
$R^3$ represents cyano, trifluoromethyl or trifluoromethoxy;
$R^4$ represents hydrogen or methyl;
such that when $R^3$ represents cyano, $R^4$ represents a group other than hydrogen.

In one embodiment of the second aspect, n represents 0 or 1. In a further embodiment, n represents 0. When present, in one embodiment of the second aspect, $R^1$ represents $C_{1-4}$ alkyl (e.g. methyl).

In one embodiment of the second aspect, m represents 0 or 1. In a further embodiment of the second aspect, m represents 1.

When present, in one embodiment of the second aspect, $R^2$ represents $C_{1-3}$ alkyl. In a further embodiment of the second aspect, $R^2$ represents methyl or ethyl. In a yet further embodiment of the second aspect, $R^2$ represents methyl.

In one embodiment of the second aspect, $R^3$ represents trifluoromethyl.

In one embodiment of the first or second aspect, the compound is selected from a compound of Examples 1 to 24, or a salt thereof.

In one embodiment of the first or second aspect, a compound is selected from:
3-[(4-{[4-(Trifluoromethyl)phenyl]sulfonyl}-1-piperazinyl)carbonyl]pyrazolo[1,5-a]pyrimidine;
3-[((2S)-2-Methyl-4-{[4-(trifluoromethyl)phenyl]sulfonyl}-1-piperazinyl)carbonyl]pyrazolo[1,5-a]pyrimidine;
3-[((3R)-3-Methyl-4-{[4-(trifluoromethyl)phenyl]sulfonyl}-1-piperazinyl)carbonyl]pyrazolo[1,5-a]pyrimidine;
3-[((3S)-3-Methyl-4-{[4-(trifluoromethyl)phenyl]sulfonyl}-1-piperazinyl)carbonyl]pyrazolo[1,5-a]pyrimidine;
3-Methyl-4-{[(3S)-3-methyl-4-(pyrazolo[1,5-a]pyrimidin-3-ylcarbonyl)-1-piperazinyl]sulfonyl}benzonitrile;
6-Methyl-3-[(4-{[4-(trifluoromethyl)phenyl]sulfonyl}-1-piperazinyl)carbonyl]pyrazolo[1,5-a]pyrimidine; and
3-[((2R)-2-Methyl-4-{[4-(trifluoromethyl)phenyl]sulfonyl}-1-piperazinyl)carbonyl]pyrazolo[1,5-a]pyrimidine;
or a salt thereof;
or a salt thereof.

In one embodiment of the first and second aspect, the compound is:
3-[((2S)-2-Methyl-4-{[4-(trifluoromethyl)phenyl]sulfonyl}-1-piperazinyl)carbonyl]pyrazolo[1,5-a]pyrimidine; or
3-[((2R)-2-Methyl-4-{[4-(trifluoromethyl)phenyl]sulfonyl}-1-piperazinyl)carbonyl]pyrazolo[1,5-a]pyrimidine;
or a salt thereof.

Certain compounds as defined in the first or second aspect may in some circumstances form acid addition salts thereof. It will be appreciated that for use in medicine compounds as defined in the first or second aspect may be used as salts, in which case the salts should be pharmaceutically acceptable. Pharmaceutically acceptable salts include those described by Berge, Bighley and Monkhouse, J. Pharm. Sci., 1977, 66, 1-19. The term "pharmaceutically acceptable salts" includes salts prepared from pharmaceutically acceptable acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

Compounds of pharmaceutically acceptable salts include those formed from maleic, fumaric, benzoic, ascorbic, pamoic, succinic, hydrochloric, sulfuric, bismethylenesalicylic, methanesulfonic, ethanedisulfonic, propionic, tartaric, salicylic, citric, gluconic, aspartic, stearic, palmitic, itaconic, glycolic, p-aminobenzoic, glutamic, benzenesulfonic, cyclohexylsulfamic, phosphoric and nitric acids.

It will be appreciated by those skilled in the art that certain protected derivatives of the compounds as defined in the first or second aspect, which may be made prior to a final deprotection stage, may not possess pharmacological activity as such, but may, in certain instances, be administered orally or parenterally and thereafter metabolized in the body to form compounds as defined in the first and second aspect which are pharmacologically active. Such derivatives may therefore be described as "prodrugs". All protected derivatives and pro-drugs of compounds defined in the first and second aspect are included within the scope of the invention. Compounds of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within the compounds as defined in the first and second aspects. Therefore, in a further aspect, the invention provides a prodrug of a compound as defined in the first and second aspect.

It will be appreciated that certain compounds as defined in the first or second aspect, or their salts, may exist as solvates, such as hydrates. Where solvates exist, this invention includes within its scope stoichiometric and non-stoichiometric solvates.

It will be appreciated that certain compounds as defined in the first or second aspect, or their salts, may exist in more than one polymorphic form. The invention extends to all such forms whether in a pure polymorphic form or when admixed with any other material, such as another polymorphic form.

Certain compounds as defined in the first or second aspect are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The subject invention also includes isotopically-labelled compounds, which are identical to the compounds as defined in the first or second aspect, but for the fact that one or more atoms are replaced by an atom having an atomic mass or mass number different from the atomic mass or mass number most commonly found in nature. Compounds of isotopes that can be incorporated into compounds of the invention include isotopes of hydrogen, carbon, nitrogen, fluorine, such as $^3$H, $^{11}$C, $^{14}$C and $^{18}$F.

Compounds as defined in the first or second aspect and salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography). PET is useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds as defined in the first or second aspect and following of this invention can generally be prepared by carrying out the procedures disclosed in the Schemes and/or in the Compounds below, by substituting a readily available isotopically labelled reagent for a non-isotopically labelled reagent. In one embodiment, compounds as defined in the first or second aspect, or salts thereof, are not isotopically labelled.

A compound of formula (I) as defined in the first or second aspect may be prepared as set forth in the following Schemes and in the experimental write-ups. The following processes form another aspect of the present invention.

Throughout the specification, general formulae are designated by Roman numerals (I), (II), (III), (IV), etc. Subsets of these general formulae are defined as (Ia), (Ib), (Ic), etc. . . . (IVa), (IVb), (IVc), etc.

The present invention also provides a process for the preparation of a compound as defined in the first or second aspect, or a salt thereof, which process comprises:

(a) reacting a compound of formula (II)

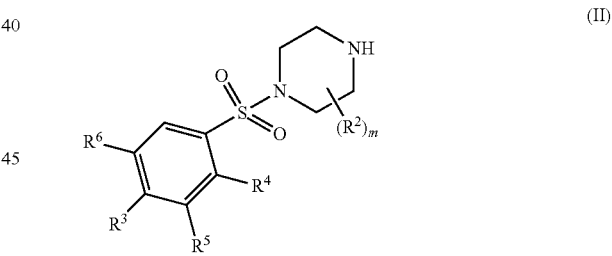

or a derivative thereof, with a compound of formula (III)

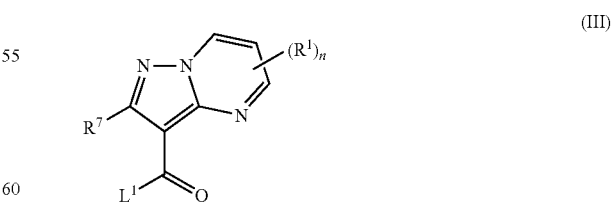

wherein $R^1$, $R^2$, $R^3$, $R^4$, $R^5$, $R^6$, $R^7$, m and n are as defined above and $L^1$ represents a suitable leaving group such as a halogen atom (e.g. chlorine or bromine) or hydroxyl group activated by commercially available amide coupling reagents (for example HOBT, HBTU and HATU);

(b) reacting a compound of formula (IV)

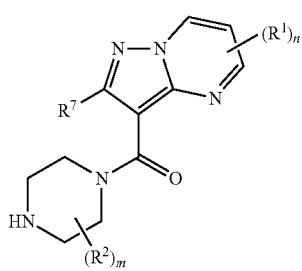

with a compound of formula (V)

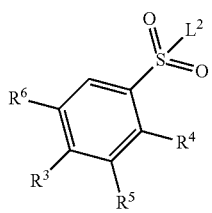

wherein $R^1$, $R^2$, $R^3$, $R^4$, $R^5$, $R^6$, $R^7$, m and n are as defined above and $L^2$ represents a suitable leaving group such as a halogen atom (e.g. chlorine or bromine);

(c) interconversion to other compounds as defined in the first or second aspect.

Process (a) typically comprises reaction of a compound of formula (II) with a compound of formula (III) in a suitable solvent such as acetonitrile, tetrahydrofuran, N,N-dimethylformamide or dichloromethane, in the presence of a suitable base, (for example, triethylamine, di-isopropylethylamine or PS-DIPEA) at 0° C. to ambient temperature (for example, room temperature).

Process (b) typically comprises reaction of a compound of formula (IV) and (V) in the presence of a suitable solvent (such as dichloromethane or acetonitrile) in the presence of a suitable base, (for example triethylamine, di-isopropylethylamine or PS-DIPEA) at 0° C. to ambient temperature (for example, room temperature). Alternatively, process (b) may typically comprise reaction of the Descriptions in the presence of a suitable base as a solvent (for example pyridine).

Process (c) may be performed using conventional interconversion procedures such as epimerization, oxidation, reduction, alkylation, nucleophilic or electrophilic aromatic substitution.

For example, a compound as defined in the first or second aspect, where $R^1$ is bromo, may be converted to a compound as defined in the first or second aspect where $R^1$ is a nitrile (cyano) group. This step typically comprises reacting the bromo compound with zinc cyanide in the presence of a palladium catalyst (for example tris(dibenzildeneacetone)dipalladium(0)) and ligand (for example 1,1'-bis(diphenylphosphino)ferrocene) in a suitable solvent (such as N,N-dimethylformamide) at elevated temperatures (such as 95° C.).

Another example of an interconversion is from a compound of formula (VII) where $R^3$ is bromo to a compound of formula (VII) where $R^3$ is a nitrile (cyano) group. This step typically comprises reacting the bromo compound with zinc cyanide in the presence of a palladium catalyst (for example tris(dibenzildeneacetone)dipalladium(0)) and ligand (for example 1,1'-bis(diphenylphosphino)ferrocene) in a suitable solvent (such as N,N-dimethylformamide) at elevated temperatures (such as 120° C.).

Compounds of formula (II) may be prepared in accordance with the following Scheme:

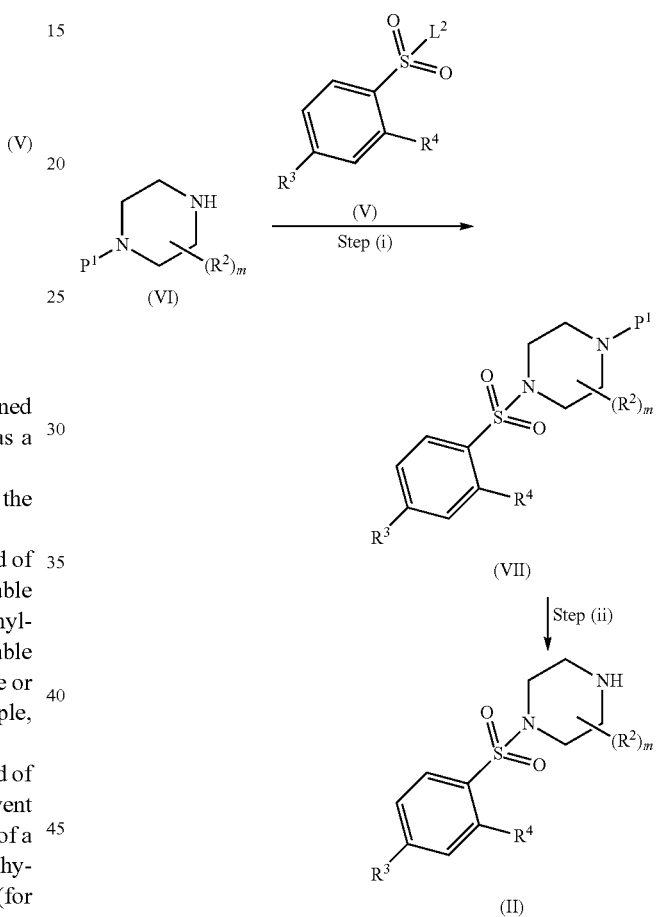

wherein $R^2$, $R^3$, $R^4$, m and $L^2$ are as defined above and $P^1$ represents a suitable protecting group such as t-butoxycarbonyl.

Step (i) typically comprises reacting a compound of formula (V) and (VI) in a suitable solvent, such as dichloromethane or acetonitrile in the presence of a base, (for example triethylamine, di-isopropylethylamine or PS-DIPEA) at 0° C. to ambient temperature (for example room temperature). Alternatively, step (i) may typically be carried out using a suitable base as a solvent (for example pyridine).

Step (ii) typically comprises a deprotection reaction. For example, when $P^1$ represents t-butoxycarbonyl, step (ii) will typically comprise treatment with an acid, for example hydrochloric acid or trifluoroacetic acid, in a solvent (such as 1,4-dioxane, dichloromethane or a mixture of methanol and 1,4-dioxane).

Compounds of formula (IV) may be prepared in accordance with the following Scheme:

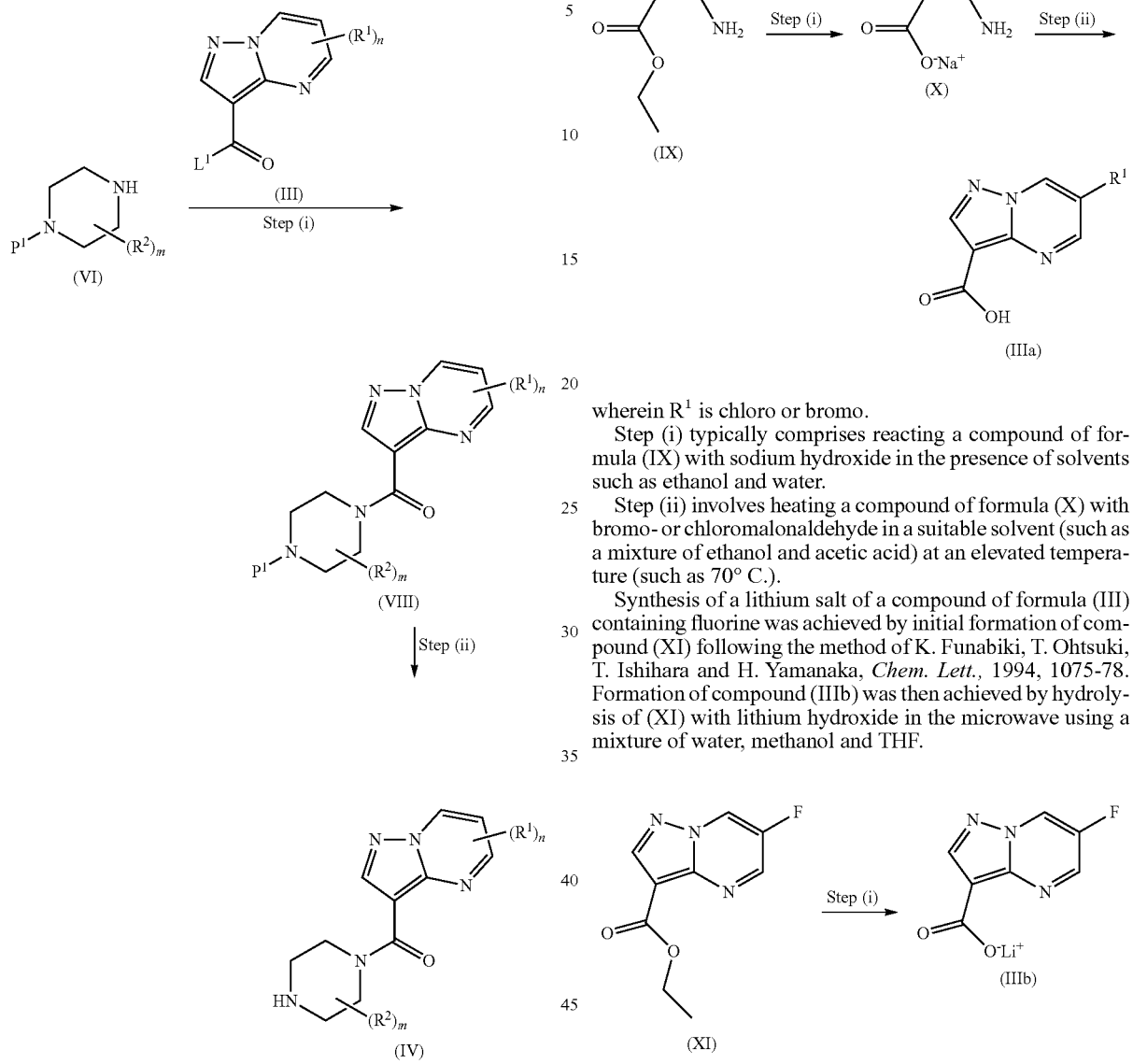

wherein $R^2$, m, $R^1$, n and $P^1$ are as defined above.

Step (i) typically comprises reacting a compound of formula (VI) with a compound of formula (III) in a suitable solvent (such as acetonitrile, tetrahydrofuran, N,N-dimethylformamide or dichloromethane) in the presence of a suitable base (for example, triethylamine, di-isopropylethylamine or PS-DIPEA) at 0° C. to ambient temperature (for example room temperature).

Step (ii) typically comprises a deprotection reaction which may be carried out in an analogous manner to Step (ii) above.

Compounds of formula (III), (V) and (VI) are either commercially available, or may be prepared by known methods.

For example, compounds of formula (III) where $R^1$ is chloro or bromo may be prepared according to the following Scheme:

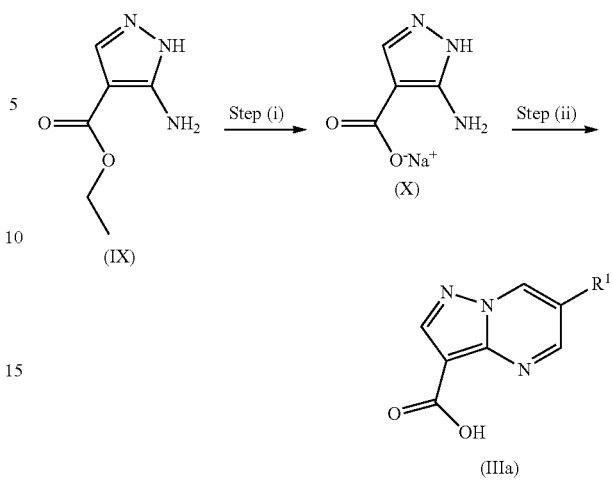

wherein $R^1$ is chloro or bromo.

Step (i) typically comprises reacting a compound of formula (IX) with sodium hydroxide in the presence of solvents such as ethanol and water.

Step (ii) involves heating a compound of formula (X) with bromo- or chloromalonaldehyde in a suitable solvent (such as a mixture of ethanol and acetic acid) at an elevated temperature (such as 70° C.).

Synthesis of a lithium salt of a compound of formula (III) containing fluorine was achieved by initial formation of compound (XI) following the method of K. Funabiki, T. Ohtsuki, T. Ishihara and H. Yamanaka, *Chem. Lett.*, 1994, 1075-78. Formation of compound (IIIb) was then achieved by hydrolysis of (XI) with lithium hydroxide in the microwave using a mixture of water, methanol and THF.

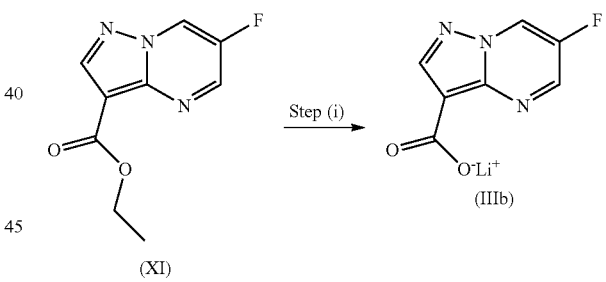

Compounds with affinity for $Ca_v2.2$ calcium channels may be useful in the treatment or prophylaxis of pain, including acute pain, chronic pain, chronic articular pain, musculoskeletal pain, neuropathic pain, inflammatory pain, visceral pain, pain associated with cancer, pain associated with migraine, tension headache and cluster headaches, pain associated with functional bowel disorders, lower back and neck pain, pain associated with sprains and strains, sympathetically maintained pain; myositis, pain associated with influenza or other viral infections such as the common cold, pain associated with rheumatic fever, pain associated with myocardial ischemia, post operative pain, cancer chemotherapy, headache, toothache and dysmenorrhea.

'Chronic articular pain' conditions include rheumatoid arthritis, osteoarthritis, rheumatoid spondylitis, gouty arthritis and juvenile arthritis.

'Pain associated with functional bowel disorders' includes non-ulcer dyspepsia, non-cardiac chest pain and irritable bowel syndrome.

'Neuropathic pain' syndromes include: diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Other conditions which could potentially be treated by compounds of the present invention include neurodegenerative diseases and neurodegeneration, neurodegeneration following trauma, tinnitus, dependence on a dependence-inducing agent such as opiods (e.g. morphine), CNS depressants (e.g. ethanol), psychostimulants (e.g. cocaine) and nicotine.

Neurodegenerative diseases include dementia, particularly degenerative dementia (including senile dementia, dementia with Lewy bodies, Alzheimer's disease, Pick's disease, Huntingdon's chorea, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection, meningitis and shingles); metabolism; toxins; anoxia and vitamin deficiency; and mild cognitive impairment associated with aging, particularly Age Associated Memory Impairment.

The compounds as defined in the first and second aspect may also be useful for neuroprotection and in the treatment or prophylaxis of neurodegeneration following trauma such as stroke, cardiac arrest, pulmonary bypass, traumatic brain injury, spinal cord injury or the like.

Another condition which could potentially be treated by compounds as defined in the first and second aspect is spasticity or muscular hypertonicity.

Hence, in a third aspect, compounds as defined in the first or second aspect, or a pharmaceutically salt thereof, are for use in therapy.

In an embodiment of the third aspect, the therapy is to the treatment or prophylaxis of any of the disorders described herein, in particular pain. In one particular embodiment, the therapy is to the treatment of any of the disorders described herein, in particular pain.

According to a further aspect, there is provided a use of a compound as defined in the first or second aspect, or a pharmaceutically acceptable salt thereof, in the manufacture of a medicament for the treatment or prophylaxis of any of the disorders herein, in particular pain. More particularly, there is provided a use of a compound of formula (I) as defined in the first and second aspect, or a pharmaceutically acceptable salt thereof, in the manufacture of a medicament for the treatment of any of the disorders herein.

According to another aspect, there is provided a method of treatment or prophylaxis of any of the disorders herein, in particular pain in humans, which method comprises the administration to the human in need of such treatment or prophylaxis, an effective amount of a compound as defined in the first or second aspect, or a pharmaceutically acceptable salt thereof.

In the context of the present invention, the term "treatment" refers to symptomatic treatment and the term "prophylaxis" is used to mean preventing symptoms in an already afflicted subject or preventing recurrence of symptoms in an afflicted subject and is not limited to complete prevention of an affliction.

In order to use a compound of formula (I) as defined in the first and second aspect or a pharmaceutically acceptable salt thereof for the treatment or prophylaxis of humans and other mammals it is normally formulated in accordance with standard pharmaceutical practice as a pharmaceutical composition. Therefore in another aspect of the invention there is provided a pharmaceutical composition comprising a compound of formula (I) as defined in the first and second aspect, or a pharmaceutically acceptable salt thereof, adapted for use in human or veterinary medicine.

In order to use the compounds as defined in the first and second aspect in therapy, they will normally be formulated into a pharmaceutical composition in accordance with standard pharmaceutical practice. The present invention also provides a pharmaceutical composition, which comprises a compound of formula (I) as defined in the first and second aspect, or a pharmaceutically acceptable salt thereof, and optionally a pharmaceutically acceptable excipient.

When used in the treatment or prophylaxis of pain, the compound of formula (I) as defined in the first and second aspect or a pharmaceutically acceptable salt thereof may be used in combination with other medicaments indicated to be useful in the treatment or prophylaxis of pain of neuropathic origin including neuralgias, neuritis and back pain, and inflammatory pain including osteoarthritis, rheumatoid arthritis, acute inflammatory pain, back pain and migraine. Such therapeutic agents include for example COX-2 (cyclooxygenase-2) inhibitors, such as celecoxib, deracoxib, rofecoxib, valdecoxib, parecoxib, COX-189 or 2-(4-ethoxyphenyl)-3-(4-methanesulfonyl-phenyl)-pyrazolo[1,5-b]pyridazine (WO99/012930); 5-lipoxygenase inhibitors; NSAIDs (non-steroidal anti-inflammatory drugs) such as diclofenac, indomethacin, nabumetone or ibuprofen; bisphosphonates, leukotriene receptor antagonists; DMARDs (disease modifying anti-rheumatic drugs) such as methotrexate; adenosine A1 receptor agonists; sodium channel blockers, such as lamotrigine; NMDA (N-methyl-D-aspartate) receptor modulators, such as glycine receptor antagonists or memantine; ligands for the $\alpha_2\delta$-subunit of voltage gated calcium channels, such as gabapentin, pregabalin and solzira; tricyclic antidepressants such as amitriptyline; neurone stabilizing antiepileptic drugs; cholinesterase inhibitors such as galantamine; mono-aminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; nicotinic acetyl choline (nACh) receptor modulators; glutamate receptor modulators, for example modulators of the NR2B subtype; $EP_4$ receptor ligands; $EP_2$ receptor ligands; $EP_3$ receptor ligands; $EP_4$ agonists and $EP_2$ agonists; $EP_4$ antagonists; $EP_2$ antagonists and $EP_3$ antagonists; cannabinoid receptor ligands; bradykinin receptor ligands; vanilloid receptor or Transient Receptor Potential (TRP) ligands; and purinergic receptor ligands, including antagonists at $P2X_3$, $P2X_{2/3}$, $P2X_4$, $P2X_7$ or $P2X_{4/7}$; KCNQ/Kv7 channel openers, such as retigabine; Additional COX-2 inhibitors are disclosed in U.S. Pat. No. 5,474,995, U.S. Pat. No. 5,633,272; U.S. Pat. No. 5,466,823, U.S. Pat. No. 6,310,099 and U.S. Pat. No. 6,291,523; and in WO 96/25405, WO 97/38986, WO 98/03484, WO 97/14691, WO99/12930, WO00/26216, WO00/52008, WO00/38311, WO01/58881 and WO02/18374.

When used in the treatment or prophylaxis of Alzheimer's disease, the compound of formula (I) as defined in the first and second aspect or a pharmaceutically acceptable salt thereof may be used in combination with other medicaments indicated to be useful as either disease modifying or symptomatic treatments of Alzheimer's disease.

Suitable Compounds of such other therapeutic agents may be agents known to modify cholinergic transmission such as 5-HT$_{1A}$ antagonists, (e.g. lecozotan), 5-HT6 antagonists, M1 muscarinic agonists, M2 muscarinic antagonist, acetylcholinesterase inhibitors (e.g tetrahydroaminoacridine, donepezil or rivastigmine), or allosteric modulators, nicotinic receptor agonists or allosteric modulators, symptomatic agents such as 5-HT6 receptor antagonists, e.g. SB742457, H3 receptor antagonists e.g. GSK189254 and GSK239512, 5-HT4 receptor agonist, PPAR agonists, also NMDA receptor antagonists or modulators, also disease modifying agents such as ~β or γ-secretase inhibitors (e.g. R-flurbiprofen), also AMPA positive modulators and Glycine Transporter Reuptake inhibitors.

When a compound of formula (I) as defined in the first and second aspect or a pharmaceutically acceptable salt thereof is used in combination with another therapeutic agent, the compounds may be administered either sequentially or simultaneously by any convenient route.

The invention thus provides, in a further aspect, a combination comprising a compound of formula (I) as defined in the first and second aspect or a pharmaceutically acceptable salt thereof together with a further therapeutic agent or agents.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilizing a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilized before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10% to 60% by weight, of the active material, depending on the method of administration. The dose of the compound of formula (I) as defined in the first and second aspect or a pharmaceutically acceptable salt thereof used in the treatment or prophylaxis of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks, months, years or even life.

A further aspect to the invention is a pharmaceutical composition comprising 0.05 to 1000 mg of a compound of formula (I) or a pharmaceutically acceptable salt thereof, and 0 to 3 g more suitably 0 to 2 g of at least one pharmaceutically acceptable carrier.

All publications, including but not limited to patents and patent applications, cited in this specification are herein incorporated by reference as if each individual publication were specifically and individually indicated to be incorporated by reference herein as though fully set forth.

Abbreviations:
Ar—argon
API—atmospheric pressure ionization
aq.—aqueous
eq.—equivalent
dba—dibenzylideneacetone
DCM—dichloromethane
DIPEA—diisopropylethylamine
DMF—N,N-dimethylformamide
DMSO—dimethylsulfoxide
DPPF—1,1'-Bis(diphenylphosphino)ferrocene
EtOAc—ethyl acetate
ES—Electrospray
HATU—o-(7-Azabenzotriazol-1-yl)-N,N,N',N'-tetramethyluronium hexafluorophosphate
HBTU—O-benzotriazole-N,N,N',N'-tetramethyl-uronium-hexafluoro-phosphate
HOBT—Hydroxybenzotriazole
HPLC—high performance liquid chromatography
LCMS—Liquid Chromatography Mass Spectrometry
MS—mass spectrometry
MeCN—acetonitrile
MDAP—mass directed automated preparative liquid chromatography.
MeOH—methanol
NMR—nuclear magnetic resonance
PS-DIPEA—polymer supported diisopropylethylamine
rt—room temperature
sat.—saturated
SCX—strong cation exchange chromatography
THF—tetrahydrofuran
TFA—trifluoroacetic acid
Pd$_2$(dba)$_3$—tris(dibenzylideneacetone)dipalladium(0)
Pd(PPh$_3$)$_4$—tetrakis(triphenylphosphine)palladium
UPLC—Ultra Performance Liquid Chromatography
h—hour(s)
min—minutes

EXAMPLES

The preparation of a number of supporting compounds as defined in the first to fourth aspect are described below.

In the procedures that follow, after each starting material, reference to a Description is typically provided. This is provided merely for assistance to the skilled chemist. The starting material may not necessarily have been prepared from the batch referred to.

Description 1

1-{[4-(Trifluoromethyl)phenyl]sulfonyl}piperazine

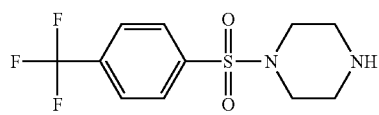

To a solution of 1,1-dimethylethyl 1-piperazinecarboxylate (5.00 g, 26.8 mmol) in DCM (200 ml) was added DIPEA (9.85 ml, 56.4 mmol) and then 4-(trifluoromethyl)benzenesulfonyl chloride (7.22 g, 29.5 mmol). The reaction mixture was stirred for 1.5 hours at rt. The reaction mixture was then reduced to dryness in vacuo, to yield 1,1-dimethylethyl 4-{[4-(trifluoromethyl)phenyl]sulfonyl}-1-piperazinecarboxylate.

m/z (API-ES) 294.72 [M+H-100]$^+$

To a solution of 1,1-dimethylethyl 4-{[4-(trifluoromethyl)phenyl]sulfonyl}-1-piperazinecarboxylate in 1,4-dioxane (100 ml) was added 4M HCl in 1,4-dioxane (50 ml, 200 mmol) and 3 drops of distilled water. The reaction mixture was stirred overnight and then reduced to dryness in vacuo. The residue was dissolved in DCM (200 ml) and washed with 2M aq. NaOH (50 ml), twice. The organic layer was dried over dried magnesium sulphate, the insolubles removed by filtration, and filtrate reduced to dryness in vacuo to yield the title compound (6.60 g) as a pale yellow solid.

m/z (API-ES) 294.74 [M+H]$^+$ $^1$H NMR (400 MHz, CHLOROFORM-d) δ ppm 2.89-2.98 (m, 4H), 2.99-3.09 (m, 4H), 3.71 (s, 1H), 7.77-7.85 (m, 2H), 7.85-7.92 (m, 2H).

Description 2

(3S)-3-Methyl-1-{[4-(trifluoromethyl)phenyl]sulfonyl}piperazine

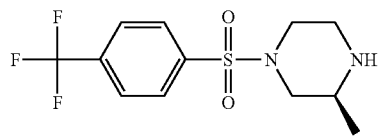

To a solution of 1,1-dimethylethyl(2S)-2-methyl-1-piperazinecarboxylate (5.00 g, 25.0 mmol) in DCM (200 ml) was added DIPEA (11.4 ml, 65.5 mmol) and 4-(trifluoromethyl)benzenesulfonyl chloride (5.68 g, 23.2 mmol). The reaction mixture was stirred for 1 hour. DCM (200 ml) was added to the reaction mixture which was transferred to a separating funnel. The solution was washed with saturated aq. sodium bicarbonate solution (50 ml, twice) and then with distilled water (50 ml). The organic layer was dried over magnesium sulphate which was removed by filtration and the filtrate was evaporated to dryness in vacuo to give 8.9 g of white solid.

The solid was dissolved in 1,4-dioxane (30 ml) and 4M HCl in 1,4-dioxane (10 ml) and a few drops of water were added and the reaction mixture was stirred for 1 hour. Further 4M HCl in 1,4-dioxane (20 ml) was added and the reaction stirred overnight.

The reaction mixture was evaporated to dryness in vacuo and the residue was dissolved in MeOH (100 ml) and loaded onto an SCX column (Biotage). The column was washed with MeOH and the product was eluted with 1M ammonia in MeOH. LCMS showed a large amount of desired product present in the MeOH wash, so this was evaporated to dryness on the rotary evaporator. The residue was dissolved in EtOAc (100 ml) and extracted with 2M HCl (50 ml). The aqueous layer was basified with 2M aq. NaOH solution until pH remained above 7 and extracted with EtOAc (100 ml). The organic layer was evaporated to dryness on the rotary evaporator to yield the title compound (4.34 g).

m/z (API-ES) 309 [M+H]$^+$ $^1$H NMR (400 MHz, MeOH-d4) δ ppm 1.36 (d, J=6.6 Hz, 3H), 2.62-2.73 (m, 1H), 2.85-2.97 (m, 1H), 3.19-3.29 (m, 1H), 3.45-3.54 (m, 2H), 3.80-3.95 (m, 2H), 7.95 (d, J=8.3 Hz, 2H), 8.05 (d, J=8.3 Hz, 2H).

Description 3

1,1-Dimethylethyl(3R)-3-methyl-4-{[4-(trifluoromethyl)phenyl]sulfonyl}-1-piperazinecarboxylate

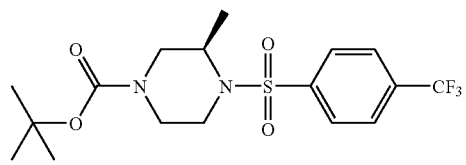

To a solution of 1,1-dimethylethyl(3R)-3-methyl-1-piperazinecarboxylate (1.50 g, 7.49 mmol) in DCM (30 ml) was added DIPEA (1.96 ml, 11.2 mmol) and then portionwise addition of 4-(trifluoromethyl)benzenesulfonyl chloride (2.20 g, 8.99 mmol) at rt. The resultant mixture was stirred under an atmosphere of argon for 2 hours before addition of 1M aq. HCl solution (75 ml) and DCM (75 ml). The layers were separated and the aqueous layer was then re-extracted with DCM (75 ml), the organic layers were combined and washed with saturated brine solution (100 ml). The organic layers were then separated, dried (MgSO$_4$) and concentrated to dryness giving the title compound (3.39 g).

m/z (API-ES) 309 [M+H-100]$^+$ $^1$H NMR (400 MHz, CHLOROFORM-d) δ ppm 1.03 (d, J=6.7 Hz, 3H) 1.43 (s, 9H) 2.65-3.22 (m, 3H) 3.54-4.27 (m, 4H) 7.78 (d, J=8.2 Hz, 2H) 7.93 (d, J=8.2 Hz, 2H).

Description 4

(2R)-2-Methyl-1-{[4-(trifluoromethyl)phenyl]sulfonyl}piperazine hydrochloride

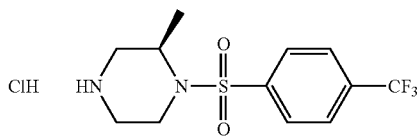

To a solution of 1,1-dimethylethyl(3R)-3-methyl-4-{[4-(trifluoromethyl)phenyl]sulfonyl}-1-piperazinecarboxylate (may be prepared as described in Description 3) (3.39 g, 8.30 mmol) in 1,4-dioxane (20 ml) was added HCl (4M in 1,4-dioxane) (10.4 ml, 41.5 mmol) and the resultant mixture stirred under an atmosphere of Ar for 16 hours. A further 5 ml of 4M HCl in dioxane was added and the mixture stirred at rt for 72 hours. The mixture was concentrated to dryness and the residue triturated with diethyl ether and the solid collected by filtration giving the title compound (2.51 g) as a white powder.

m/z (API-ES) 309 [M+H]$^+$ $^1$H NMR (400 MHz, DMSO-d$_6$) δ ppm 1.16 (d, J=7.0 Hz, 3H), 2.72-2.86 (m, 1H), 2.96 (dd, J=13.0, 4.28 Hz, 1H), 3.08-3.24 (m, 2H), 3.26-3.34 (m, 1H), 3.70-3.84 (m, 1H), 4.16-4.32 (m, 1H), 8.03 (d, J=8.4 Hz, 2H), 8.09 (d, J=8.3 Hz, 2H), 9.16 (br. s. 2H).

Description 5

1,1-Dimethylethyl(3S)-3-methyl-4-{[4-(trifluoromethyl)phenyl]sulfonyl}-1-piperazinecarboxylate

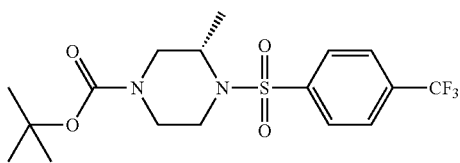

To a solution of 1,1-dimethylethyl(3S)-3-methyl-1-piperazinecarboxylate (2.05 g, 10.2 mmol) in DCM (50 ml) was added DIPEA (2.68 ml, 15.4 mmol) and the mixture stirred at rt for 10 minutes before addition of 4-(trifluoromethyl)benzenesulfonyl chloride (3.00 g, 12.3 mmol) at 0° C. The resultant mixture stirred under an atmosphere of argon for 16 hours before addition of water (50 ml) and DCM (30 ml). The layers were separated using a hydrophobic frit and the organic layers concentrated to dryness giving the title compound (4.40 g) as a white solid.

m/z (API-ES) 309 [M+H-100]$^+$

1H NMR (400 MHz, CHLOROFORM-d) δ ppm 1.03 (d, J=6.7 Hz, 3H), 1.43 (s, 9H), 2.59-3.33 (m, 3H), 3.43-4.35 (m, 4H), 7.77 (d, J=8.2 Hz, 2H), 7.93 (d, J=8.2 Hz, 2H).

Description 6

(2S)-2-Methyl-1-{[4-(trifluoromethyl)phenyl]sulfonyl}piperazine hydrochloride

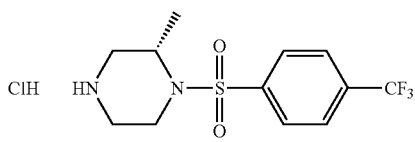

To a solution of 1,1-dimethylethyl(3S)-3-methyl-4-{[4-(trifluoromethyl)phenyl]sulfonyl}-1-piperazinecarboxylate (may be prepared as described in Description 5) (4.40 g, 10.8 mmol) in 1,4-dioxane (30 ml) was added HCl (4M in 1,4-dioxane) (5.39 ml, 21.6 mmol) and the mixture stirred at rt for 2 hours. A further portion of HCl (4M in 1,4-dioxane) (16.2 ml, 64.6 mmol) was then added and the mixture stirred for a further 16 hours. The volatiles were then removed in vacuo to give the title compound (3.80 g) as a white solid.

m/z (API-ES) 309 [M+H]$^+$

1H NMR (400 MHz, MeOH-d4) δ ppm 1.20 (d, J=7.1 Hz, 3H), 2.95-3.25 (m, 3H), 3.36-3.45 (m, 1H), 3.56-3.77 (m, 1H), 3.87-4.00 (m, 1H), 4.34-4.51 (m, 1H), 4.34-4.51 (m, 1H), 7.94 (d, J=8.3 Hz, 2H), 8.08 (d, J=8.3 Hz, 2H).

Description 7

1,1-Dimethylethyl(2S)-4-[(4-bromo-2-methylphenyl)sulfonyl]-2-methyl-1-piperazinecarboxylate

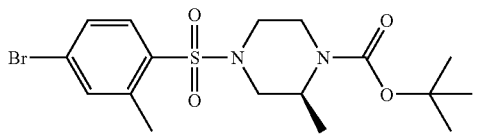

To a solution of 1,1-dimethylethyl(2S)-2-methyl-1-piperazinecarboxylate (2.00 g, 9.99 mmol) and DIPEA (2.62 ml, 15.0 mmol) in dry DCM (25 ml) at 0° C. under Ar was added 4-bromo-2-methylbenzenesulfonyl chloride (2.96 g, 11.0 mmol) and the resulting yellow solution allowed to warm to rt, then stirred at rt for 18 hours. Saturated aq. NH$_4$Cl (40 ml) was added, then the aqueous layer was extracted with DCM (30 ml). The combined organic layers were passed through a hydrophobic frit, then concentrated in vacuo to give a yellow oil (5.01 g). Flash chromatography (silica; Flash 40M; linear gradient (6-50%) EtOAc in isohexane) gave the title compound as a very pale yellow oil 1,1-dimethylethyl(2S)-4-[(4-bromo-2-methylphenyl)sulfonyl]-2-methyl-1-piperazinecarboxylate (3.52 g).

m/z (API-ES) 333 and 335, 1:1, [M+H-100]$^+$

1H NMR (400 MHz, CHLOROFORM-d) δ ppm 1.19 (d, J=6.7 Hz, 3H), 1.44 (s, 9H), 2.59 (td, J=12.0, 3.4 Hz, 1H), 2.61 (s, 3H), 2.78 (dd, J=12.0, 3.8 Hz, 1H), 3.11 (td, J=12.0, 3.2 Hz, 1H), 3.44 (dt, J=12.0, 2.0 Hz, 1H), 3.59-3.65 (m, 1H), 3.93 (d, J=12.0 Hz, 1H), 4.33 (br. s., 1H), 7.45-7.51 (m, 2H), 7.72 (d, J=8.4 Hz, 1H).

Description 8

1,1-Dimethylethyl(2S)-4-[(4-cyano-2-methyl phenyl)sulfonyl]-2-methyl-1-piperazinecarboxylate

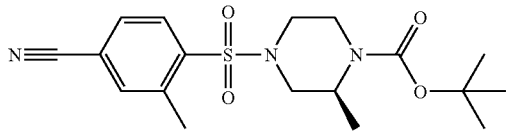

Ar was bubbled through a solution of 1,1-dimethylethyl (2S)-4-[(4-bromo-2-methylphenyl)sulfonyl]-2-methyl-1-piperazinecarboxylate (may be prepared as described in Description 7) (3.51 g, 8.10 mmol) in dry DMF (40 ml) for 0.5 hours, then $Zn(CN)_2$ (0.523 g, 4.45 mmol), $Pd_2(dba)_3$ (0.223 g, 0.243 mmol) and DPPF (0.269 g, 0.486 mmol) were added and the resulting brown solution stirred at 120° C. under Ar for 2.5 hours. The mixture was cooled to rt, concentrated in vacuo and the residue partitioned between DCM (100 ml) and water (100 ml). The aqueous layer was extracted with DCM (2×100 ml), then the combined organic layers passed through a hydrophobic frit. Concentration gave a brown residue (4.31 g). Flash chromatography (silica; Flash 40M; linear gradient (6-50%) EtOAc in isohexane) gave the title compound as a yellow solid (2.88 g).

m/z (API-ES) 280 [M+H-100]$^+$

1H NMR (400 MHz, CHLOROFORM-d) δ ppm 1.20 (d, J=6.8 Hz, 3H), 1.44 (s, 9H), 2.65 (td, J=12.0, 3.4 Hz, 1H), 2.68 (s, 3H), 2.86 (dd, J=12.0, 4.2 Hz, 1H), 3.13 (td, J=12.0, 2.8 Hz, 1H), 3.49 (dt, J=12.0, 1.8 Hz, 1H), 3.63-3.69 (m, 1H), 3.95 (d, J=12.0 Hz, 1H), 4.35 (br. s., 1H), 7.61-7.65 (m, 2H), 7.96 (d, J=6.8 Hz, 1H).

Description 9

3-Methyl-4-{[(3S)-3-methyl-1-piperazinyl]sulfonyl}benzonitrile

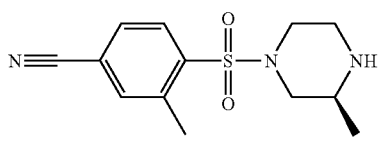

A solution of 1,1-dimethylethyl(2S)-4-[(4-cyano-2-methylphenyl)sulfonyl]-2-methyl-1-piperazinecarboxylate (may be prepared as described in Description 8) (2.88 g, 7.59 mmol) and TFA (10 ml, 130 mmol) in dry DCM (10 ml) was stirred at rt for 1 hour, then concentrated in vacuo, azetroping with toluene (25 ml) to give a brown oil. This was partitioned between DCM (50 ml) and sat. aq. $NaHCO_3$ (50 ml), then the aq. layer extracted with DCM (50 ml). The combined organic layers were passed through a hydrophobic frit and concentrated in vacuo to give the title compound as a yellow oil (2.29 g).

m/z (API-ES) 280 [M+H]$^+$

1H NMR (400 MHz, CHLOROFORM-d) δ ppm 1.06 (d, J=6.4 Hz, 3H), 2.33 (dd, J=11.6, 10.2 Hz, 1H), 2.67 (s, 3H), 2.69-2.75 (td, J=11.5, 3.1 Hz, 1H), 2.82-2.92 (m, 2H), 3.03 (dt, J=12.1, 2.6 Hz, 1H), 3.54-3.65 (m, 2H), 7.59-7.67 (m, 2H), 7.99 (d, J=8.6 Hz, 1H).

Description 10

(3R)-3-Methyl-1-{[4-(trifluoromethyl)phenyl]sulfonyl}piperazine

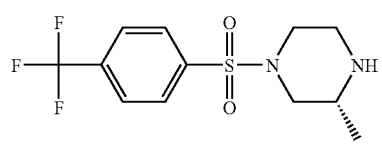

To a solution of 1,1-dimethylethyl(2R)-2-methyl-1-piperazinecarboxylate (2.95 g, 14.7 mmol) in DCM (120 ml) was added DIPEA (5.40 ml, 30.9 mmol) and then 4-(trifluoromethyl)benzenesulfonyl chloride (3.96 g, 16.2 mmol). The reaction mixture was stirred 2.5 hours at rt then washed with water (250 ml), dried on a phase separation cartridge and concentrated in vacuo. The obtained product was dissolved in 1,4-dioxane (60 ml) and treated with 4M HCl in 1,4-dioxane (18.4 ml, 73.6 mmol) overnight. The mixture was concentrated in vacuo then dissolved in EtOAc (150 ml), washed with 2N aq. NaOH solution (200 ml) then dried on a phase separation cartridge and concentrated in vacuo. The product was then dissolved in EtOAc (100 ml) and extracted with 2M HCl (2×200 ml). 2M NaOH solution were added to aqueous layer until basic pH then the product was extracted with EtOAc (500 ml). The organic layer was dried on a phase separation cartridge and concentrated in vacuo to give the title compound (3.76 g).

m/z (API-ES) 309 [M+H]$^+$

1H NMR (400 MHz, CHLOROFORM-d) δ ppm 1.05 (d, J=6.4 Hz, 3H), 1.93 (t, J=10.6 Hz, 1H), 2.31 (td, J=11.2, 3.4 Hz, 1H), 2.86-3.08 (m, 3H), 3.59-3.73 (m, 2H), 7.82 (d, J=8.3 Hz, 2H), 7.89 (d, J=8.3 Hz, 2H).

Description 11

1-({4-[(trifluoromethyl)oxy]phenyl}sulfonyl)piperazine

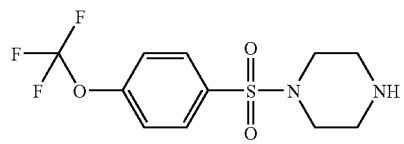

To a solution of 1,1-dimethylethyl 1-piperazinecarboxylate (5 g, 26.8 mmol) in DCM (200 ml) was added DIPEA (9.85 ml, 56.4 mmol) and then 4-[(trifluoromethyl)oxy]benzenesulfonyl chloride (4.55 ml, 26.8 mmol). The reaction mixture was stirred for 1.5 hours at rt. The reaction mixture was then evaporated to dryness in vacuo. The residue was then dissolved in 1,4-dioxane (100 ml) and 4M HCl in 1,4-dioxane (50 ml) was added, along with a few drops of distilled water. The reaction mixture was stirred for 3 hrs. Then the reaction mixture was evaporated to dryness in vacuo. The residue was dissolved in DCM (200 ml) and washed with 2M aq. NaOH (50 ml, twice). The organic layer was dried over anhydrous magnesium sulphate, the solid removed by filtration, and filtrate evaporated to dryness in vacuo. The residue was not a solid so was dissolved in ether and evaporated in vacuo to remove any remaining solvent. The title compound (8.02 g) was obtained as a pale yellow solid.

m/z (API-ES) 311 [M+H]+

1H NMR (400 MHz, CHLOROFORM-d) δ ppm 2.92-2.98 (m, 4H), 2.98-3.04 (m, 4H), 3.60-3.80 (m, 1H), 7.37 (d, J=8.9 Hz, 2H), 7.73-7.88 (d, J=8.9 Hz, 2H).

Description 12

(2R)-2-methyl-1-({4-[(trifluoromethyl)oxy]phenyl}sulfonyl)piperazine hydrochloride

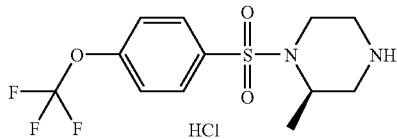

To a solution of 1,1-dimethylethyl(3R)-3-methyl-1-piperazinecarboxylate (605 mg, 2.56 mmol) in DCM (20 ml) was added DIPEA (1.12 ml, 6.39 mmol) and then portionwise 4-[(trifluoromethyl)oxy]benzenesulfonyl chloride (0.455 ml, 2.68 mmol) at room temp and the resultant mixture stirred under Ar for 16 h. DCM (75 ml) and a 1M HCl solution (75 ml) were added, the layers were separated and the organic layer was then washed with 2M NaOH solution (75 ml), the organic layers were separated, dried (MgSO₄) and concentrated to dryness. 1,1-Dimethylethyl(3R)-3-methyl-4-({4-[(trifluoromethyl)oxy]phenyl}sulfonyl)-1-piperazinecarboxylate was isolated as a slowly crystallizing white solid.

The solid was redissolved in 1,4-dioxane (4 ml), then HCl was added (4M in 1,4-dioxane, 2.59 ml, 10.4 mmol) and the resultant mixture stirred under an atmosphere of Ar for 2 h. After this time a white precipitate had formed. MeOH (5 ml) was added and the reaction stirred for a further 30 min. The reaction was concentrated to dryness giving a white solid which was triturated with Et₂O and isolated by filtration under vacuum to leave the title compound as a white solid (879 mg).

m/z (API-ES) 325 [M+H]+

¹H NMR (400 MHz, DMSO-d₆) δ ppm 1.15 (d, J=7.0 Hz, 3H), 2.80 (td, J=12.3, 3.7 Hz, 1H), 2.95 (dd, J=12.9, 4.4 Hz, 1H), 3.14 (t, J=14.3 Hz, 2H), 3.24-3.32 (m, 1H), 3.74 (d, J=14.0 Hz, 1H), 4.16-4.25 (m, 1H), 7.63 (d, J=8.1 Hz, 2H), 8.01 (m, J=8.8 Hz, 2H), 9.18 (br. s., 2H)

Description 13

(3S)-3-methyl-1-({4-[(trifluoromethyl)oxy]phenyl}sulfonyl)piperazine

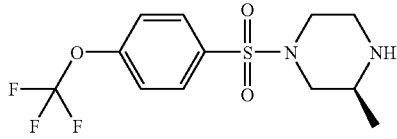

To a solution of 1,1-dimethylethyl(2S)-2-methyl-1-piperazinecarboxylate (2.50 g, 12.5 mmol), DIPEA (4.58 ml, 26.2 mmol) and 4-[(trifluoromethyl)oxy]benzenesulfonyl chloride (3.25 g, 12.5 mmol) in DCM (200 ml) was stirred at room temperature overnight. The mixture was washed with saturated aqueous NaHCO₃, then brine and concentrated under vacuum. The residue was redissolved in 1,4-dioxane (200 ml), then 4M HCl in dioxane (20 ml) and water (0.5 ml) were added and the mixture stirred overnight. The mixture was concentrated under vacuum and applied to an SCX-2 cartridge (20 g) washing with MeOH. The product was eluted with 0.5M NH₃ in MeOH; concentration left the title compound as a white solid (2.56 g).

m/z (API-ES) 325 [M+H]+

¹H NMR (400 MHz, CHLOROFORM-d) δ ppm 1.04 (d, J=6.4 Hz, 3H), 1.93 (t, J=10.6 Hz, 1H), 2.31 (td, J=11.2, 3.4 Hz, 1H), 2.86-3.07 (m, 3H), 3.58-3.68 (m, 2H), 7.37 (d, J=8.9 Hz, 2H), 7.77-7.84 (m, 2H)

Description 14

(3R)-3-methyl-1-({4-[(trifluoromethyl)oxy]phenyl}sulfonyl)piperazine

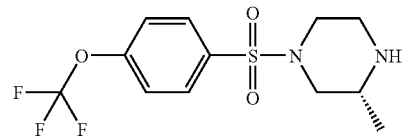

To a solution of 1,1-dimethylethyl(2R)-2-methyl-1-piperazinecarboxylate (2.00 g, 9.99 mmol) in DCM (200 ml) was added DIPEA (3.66 ml, 20.97 mmol) and then 4-[(trifluoromethyl)oxy]benzenesulfonyl chloride (1.69 ml, 9.99 mmol) and the resulting mixture stirred at room temperature for 90 min. The reaction mixture was then concentrated under vacuum and redissolved in 1,4-dioxane (100 ml). A 4M solution of HCl in 1,4-dioxane (100 ml, 400 mmol) and a few drops of distilled water were added and the mixture stirred for 3 h. The reaction mixture was concentrated under vacuum, redissolved in DCM (200 ml) and washed with 2M aqueous NaOH (2×50 ml). The organic layer was dried (MgSO₄), filtered and concentrated under vacuum. The residue was dissolved in ether and concentrated under vacuum. The oil was dissolved in MeOH (150 ml), applied to an SCX cartridge (50 g), which was washed with MeOH, DCM and MeOH again. The product was eluted from the column with 2M ammonia in methanol, DCM and then 2M ammonia in methanol; concentration under vacuum left the title compound as a transparent yellow oil (2.92 g).

m/z (API-ES) 325 [M+H]+

¹H NMR (400 MHz, CHLOROFORM-d) δ ppm 1.04 (d, J=6.4 Hz, 3H), 1.93 (t, J=10.6 Hz, 1H), 2.31 (td, J=11.2, 3.5 Hz, 1H), 2.86-3.07 (m, 3H), 3.58-3.69 (m, 2H), 7.37 (d, J=8.1 Hz, 2H), 7.77-7.85 (m, 2H)

Description 15

Ethyl 6-fluoropyrazolo[1,5-a]pyrimidine-3-carboxylate

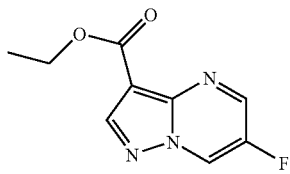

A solution of (2Z)-3-(diethylamino)-2-fluoro-2-propenal (660 mg, 4.55 mmol—synthesized according to the literature procedure: K. Funabiki, T. Ohtsuki, T. Ishihara and H. Yamanaka, *Chem. Lett.,* 1994, 1075-78.) and ethyl 3-amino-1H-pyrazole-4-carboxylate (1058 mg, 6.82 mmol) in acetic acid (5 ml) was heated at reflux for 1 h. Additional ethyl 3-amino-1H-pyrazole-4-carboxylate (200 mg) was added and the solution heated at reflux for a further 1 h. Concentration under vacuum gave a pale yellow solid that was suspended in DCM (25 ml) and 2M aqueous NaOH (25 ml). The organic layers were isolated using a phase separator, then washed with 2M aqueous HCl (25 ml), and isolated using a phase separator. Concentration under vacuum gave a pale yellow solid (530 mg). Flash chromatography (silica; Flash 12M; 2% [2M $NH_3$ in MeOH] in DCM) and concentration of the desired fractions gave the title compound as a pale yellow solid (464 mg).

m/z (API-ES) 325 [M+H]$^+$ $^1$H NMR (400 MHz, CHLOROFORM-d) δ ppm 1.42 (t, J=7.1 Hz, 3H), 4.45 (q, J=7.1 Hz, 2H), 8.60 (s, 1H), 8.72 (dd, J=3.6, 2.7 Hz, 1H), 8.82 (d, J=2.7 Hz, 1H)

$^{19}$F NMR (377 MHz, CHLOROFORM-d) δ ppm −149.6 (s)

Description 16

Lithium 6-fluoropyrazolo[1,5-a]pyrimidine-3-carboxylate

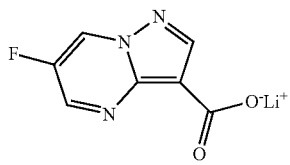

A suspension of ethyl 6-fluoropyrazolo[1,5-a]pyrimidine-3-carboxylate (512 mg, 2.45 mmol) and lithium hydroxide (61.5 mg, 2.57 mmol) in water (1 ml), MeOH (1 ml) and THF (1 ml) was irradiated to 100° C. for 10 min in the microwave. The reaction mixture was concentrated under vacuum, azeotroping with toluene (10 ml) to leave the title compound as a yellow powder (497 mg). This crude material was used directly in the subsequent reactions.

Description 17

6-bromopyrazolo[1,5-a]pyrimidine-3-carboxylic Acid

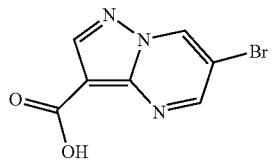

A solution of ethyl 5-amino-1H-pyrazole-4-carboxylate (2 g, 12.89 mmol) and sodium hydroxide (19.34 mL, 38.7 mmol) (aqueous, 2M) in ethanol (30 mL) was heated at 80° C. overnight. The reaction mixture was concentrated in vacuo to give a crude mixture of carboxylate and sodium hydroxide. The crude mixture was dissolved in ethanol (4 mL) and acetic acid (14 mL, 245 mmol). Whilst stirring the mixture, bromomalonaldehyde (1.947 g, 12.90 mmol) was added and then the mixture heated to 70° C. for 1 h. The reaction mixture was allowed to cool and the precipitate was filtered and washed with ethanol. The solid product was dried in a vacuum oven to give the title compound (1.589 g).

m/z (API-ES) 242+244 (1:1) [M+H]$^+$

1H NMR (400 MHz, DMSO-d$_6$) δ ppm 8.58 (s, 1H), 8.88 (d, J=2.0 Hz, 1H), 9.76 (d, J=2.0 Hz, 1H), $CO_2H$ too broad to observe.

Description 18

6-chloropyrazolo[1,5-a]pyrimidine-3-carboxylic Acid

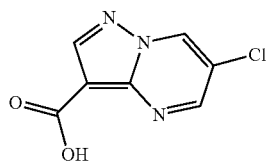

The preparation is similar to the one described in Description 17.

m/z (API-ES) 198+200 (3:1) [M+H]$^+$

Description 19

1,1-dimethylethyl(2S)-4-{[2-bromo-5-(trifluoromethyl)phenyl]sulfonyl}-2-methyl-1-piperazinecarboxylate

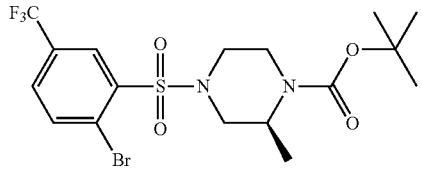

To a solution of 1,1-dimethylethyl(2S)-2-methyl-1-piperazinecarboxylate (1.18 g, 4.98 mmol) in dichloromethane (40 ml) was added DIPEA (2.70 ml, 15.45 mmol) and then 2-bromo-5-(trifluoromethyl)benzenesulfonyl chloride (1.613 g, 4.98 mmol). The reaction mixture was stirred for 1 h 20 min at room temperature, and then washed with water (50 ml), dried on a phase separation cartridge and concentrated under vacuum to give the crude title compound (2.5 g) used directly in the next step.

m/z (API-ES) 387+389 (1:1) [(M-Boc)+H]+

Description 20

1,1-dimethylethyl(2S)-2-methyl-4-{[2-methyl-5-(trifluoromethyl)phenyl]sulfonyl}-1-piperazinecarboxylate

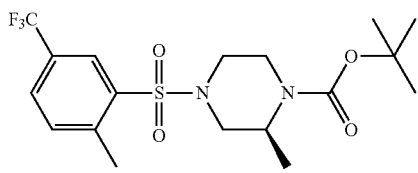

1,1-dimethylethyl(2S)-4-{[2-bromo-5-(trifluoromethyl)phenyl]sulfonyl}-2-methyl-1-piperazinecarboxylate (may be prepared as described in Description 19) (2.5 g, 5.13 mmol), potassium carbonate (1.134 g, 8.21 mmol) in 1,4-dioxane (80 ml) were stirred for 5 min then trimethylboroxin (1.142 ml, 8.21 mmol) and Pd(PPh₃)₄ (0.593 g, 0.513 mmol) were added and the reaction mixture heated at 100° C. for 1.5 h. Further trimethylboroxin (0.5 mL) was added and the reaction heated for 30 min before it was allowed to cool overnight.

The mixture was concentrated under vacuum then EtOAc (120 ml) added, washed with 200 ml of water, dried on a phase separation cartridge and evaporated under vacuum. Crude material (2.8 g) purified via Biotage (40+M silica column) using a gradient EtOAc/i-Hex from 0/100 to 30/70. Desired fractions collected and concentrated under vacuum to give the title compound (2.1 g).

m/z (API-ES) 323 [(M-Boc)+H]+

Description 21

(3S)-3-methyl-1-{[2-methyl-5-(trifluoromethyl)phenyl]sulfonyl}piperazine

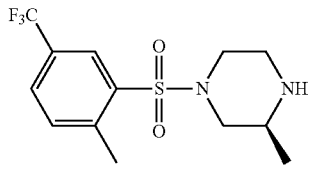

1,1-dimethylethyl(2S)-2-methyl-4-{[2-methyl-5-(trifluoromethyl)phenyl]sulfonyl}-1-piperazinecarboxylate (may be prepared as described in Description 20) (2.1 g, 4.97 mmol) in 1,4-Dioxane (50 mL) was treated by HCl 4M in dioxane (6.21 mL, 24.85 mmol). The reaction mixture was stirred overnight at room temperature. LCMS showed a 1:1 ratio between starting material and expected product. HCl 4M in dioxane (6.21 mL, 24.85 mmol) is added and the reaction mixture stirred for 4 h. LCMS showed about 10% of remaining starting material. HCl 4M in dioxane (6.21 mL, 24.85 mmol) is added and the reaction mixture stirred for 1 h.

The reaction mixture was then concentrated under vacuum, dissolved in EtOAc (100 ml) and extracted with 2N HCl (3×75 ml). 2N NaOH was added to the aqueous until basic then product extracted with EtOAc, dried on a phase separation cartridge and concentrated under vacuum to give the title compound (1.16 g).

m/z (API-ES) 323 [M+H]+

Description 22

1,1-dimethylethyl 4-{[2-bromo-5-(trifluoromethyl)phenyl]sulfonyl}-1-piperazinecarboxylate

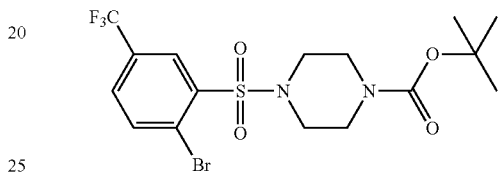

To a solution of 1,1-dimethylethyl 1-piperazinecarboxylate (1 g, 5.37 mmol) in dichloromethane (40 ml) was added DIPEA (1.969 ml, 11.28 mmol) and then 2-bromo-5-(trifluoromethyl)benzenesulfonyl chloride (1.737 g, 5.37 mmol). The mixture was stirred for 1 h 20 at room temperature before it was washed with water (50 ml), dried on a phase separation cartridge and concentrated under vacuum.

Crude product was dissolved in MeOH and eluted through a 10 g SCX cartridge (elution with MeOH), concentrated under vacuum to give the title compound (2.59 g).

m/z (API-ES) 373+375 (1:1) [(M-Boc)+H]+

Description 23

1,1-dimethylethyl 4-{[2-methyl-5-(trifluoromethyl)phenyl]sulfonyl}-1-piperazinecarboxylate

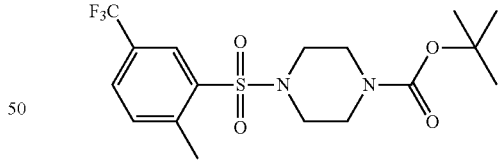

1,1-dimethylethyl 4-{[2-bromo-5-(trifluoromethyl)phenyl]sulfonyl}-1-piperazinecarboxylate (may be prepared as described in Description 22) (2.59 g, 5.47 mmol), potassium carbonate (1.513 g, 10.94 mmol) in 1,4-dioxane (80 ml) were stirred for 5 min then trimethylboroxin (1.523 ml, 10.94 mmol) and Pd(PPh₃)₄ (0.632 g, 0.547 mmol) were added and the reaction mixture heated at 100° C. for 1.5 h. Further trimethylboroxin (0.5 mL) was added and the mixture heated at 100° C. for 30 min before allowing to cool overnight. The mixture was concentrated under vacuum then EtOAc (150 ml) added, washed with 200 ml of water, dried on a phase separation cartridge and evaporated under vacuum. Crude material (3.1 g) purified via Biotage (40+M silica column) using a gradient EtOAc/i-hex from 10/90 to 30/70. Desired fractions were collected and concentrated under vacuum to give the title compound (2.1 g).
m/z (API-ES) 309 [(M-Boc)+H]⁺

Description 24

1-{[2-methyl-5-(trifluoromethyl)phenyl]sulfonyl}piperazine

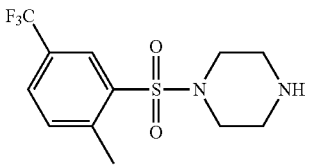

1,1-dimethylethyl 4-{[2-methyl-5-(trifluoromethyl)phenyl]sulfonyl}-1-piperazinecarboxylate (may be prepared as described in Description 23) (2.1 g, 5.14 mmol) in 1,4-dioxane (50 mL) was treated by HCl 4M in dioxane (6.43 mL, 25.7 mmol). The reaction mixture was stirred overnight at room temperature. LCMS showed a mixture of starting material and product so 8 ml of HCl 4M in dioxane were added. LCMS after 2 h showed still some starting material so 5 ml of HCl 4M in dioxane were added. LCMS after 2 h showed traces of starting material.

The reaction mixture was concentrated under vacuum, dissolved in EtOAc (70 ml) and extracted with 2N HCl (3×80 ml). 2N NaOH was added to the aqueous until basic, then product extracted with EtOAc, dried on a phase separation cartridge and concentrated under vacuum to give the title compound (1.38 g).
m/z (API-ES) 309 [M+H]⁺

Description 25

(2S)-2-methyl-1-({4-[(trifluoromethyl)oxy]phenyl}sulfonyl)piperazine hydrochloride

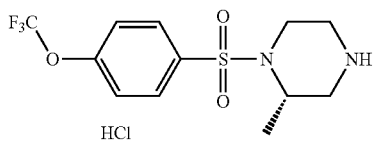

To a solution of 1,1-dimethylethyl(3S)-3-methyl-1-piperazinecarboxylate (500 mg, 2.497 mmol) in dichloromethane (20 ml) was added DIPEA (0.654 ml, 3.74 mmol) and then portionwise addition of 4-[(trifluoromethyl)oxy]benzenesulfonyl chloride (0.445 ml, 2.62 mmol) at room temperature and the resultant mixture stirred under an atmosphere of argon for 16 hours. The reaction was worked up by the addition of 1M HCl solution (75 mL) and dichloromethane (75 mL), the layers were separated and the organic layer was then washed with 2M NaOH solution (75 mL). The organic phase was separated, dried (MgSO₄) and concentrated to dryness to give 1,1-dimethylethyl(3S)-3-methyl-4-({4-[(trifluoromethyl)oxy]phenyl}sulfonyl)-1-piperazinecarboxylate (963 mg, 2.269 mmol). This was dissolved in 1,4-dioxane (4 mL), HCl (4M in 1,4-Dioxane) (2.269 mL, 9.08 mmol) was added and the resultant mixture stirred under an atmosphere of argon for 2 h. After this time a white precipitate had formed so methanol (5 ml) was added to solubilize the precipitate and the reaction stirred for a further 30 min. The reaction was concentrated to dryness giving a white solid which was triturated with Et₂O and the solid isolated by filtration under vacuum to give the title compound (585 mg).
m/z (API-ES) 325 [M+H]⁺

Description 26

1,1-dimethylethyl(2S)-4-{[2-bromo-4-(trifluoromethyl)phenyl]sulfonyl}-2-methyl-1-piperazinecarboxylate

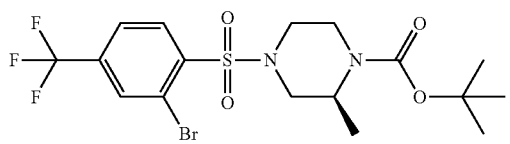

To a solution of 1,1-dimethylethyl(2S)-2-methyl-1-piperazinecarboxylate (1.20 g, 5.99 mmol) and DIPEA (5.45 ml, 31.2 mmol) in dry DCM (60 ml) at 0° C. under Ar was added 2-bromo-4-(trifluoromethyl)benzenesulfonyl chloride (2.04 g, 6.29 mmol) and the resulting clear solution stirred at 0° C. for 2 h. EtOAc (100 ml) and saturated aqueous NaHCO₃ (100 ml) were added, the layers separated, then the organic layer washed with 2M aqueous HCl (100 ml) and passed through an hydrophobic frit. The solvent was removed to leave the title compound (2.36 g).
m/z (API-ES) 387 and 389 [M+H-100]⁺
¹H NMR (400 MHz, DMSO-d₆) δ ppm 1.02 (d, J=6.7 Hz, 3H), 1.38 (s, 9H), 2.83 (td, J=12.3, 3.4 Hz, 1H), 3.00 (dd, J=12.6, 3.8 Hz, 1H), 3.07 (td, J=12.8, 3.0 Hz, 1H), 3.45 (d, J=12.6 Hz, 1H), 3.73 (d, J=12.2 Hz, 1H), 3.81 (d, J=12.8 Hz, 1H), 4.15-4.24 (m, 1H), 7.99 (dd, J=8.2, 1.3 Hz, 1H), 8.18 (d, J=8.2 Hz, 1H), 8.30 (d, J=1.1 Hz, 1H)

Description 27

(3S)-3-methyl-1-{[2-methyl-4-(trifluoromethyl)phenyl]sulfonyl}piperazine

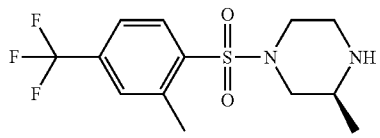

A solution of 1,1-dimethylethyl(2S)-4-{[2-bromo-4-(trifluoromethyl)phenyl]sulfonyl}-2-methyl-1-piperazinecarboxylate (1.00 g, 2.05 mmol) (may be prepared as described in Description 26), potassium carbonate (0.737 g, 5.34 mmol) in 1,4-dioxane (43 ml) were stirred for 5 min then trimethylboroxin (0.743 ml, 5.34 mmol) and Pd(Ph₃P)₄ (0.403 g, 0.349 mmol) were added and the reaction mixture heated at 100° C. overnight. EtOAc (100 ml) was added then the mixture washed aqueous sodium bicarbonate (100 ml), water (100 ml) and concentrated under vacuum. Flash chromatography (silica; linear gradient (0-20%) EtOAc in isohexane) gave 1,1-dimethylethyl(2S)-2-methyl-4-{[2-methyl-4-(trifluoromethyl)phenyl]sulfonyl}-1-piperazinecarboxylate (0.785 g).

This material was redissolved in DCM (10 ml) and 1,4-dioxane (3 ml), then HCl in dioxane (5 eq) was added and the mixture stirred at room temperature for 4 h. Aqueous sodium bicarbonate (20 ml) and EtOAc (20 ml) were added and the organic phase washed with aqueous sodium bicarbonate (2×10 ml), brine (10 ml) and dried using a hydrophobic frit. The solvent was removed under vacuum. The residue was redissolved in DCM (10 ml) and 1,4-dioxane (3 ml), then 4M HCl in 1,4-dioxane (6.97 mL, 27.9 mmol) added. The mixture was stirred at room temperature for 4 h. The solvent was evaporated under vacuum to give the title compound (0.615 g) as the hydrochloride salt.

m/z (API-ES) 323 [M+H]$^+$ $^1$H NMR (400 MHz, DMSO-d$_6$) δ ppm 1.22 (d, J=6.5 Hz, 3H), 2.66 (s, 3H), 2.77 (dd, J=12.8, 10.5 Hz, 1H), 2.93-3.11 (m, 2H), 3.29-3.39 (m, 2H), 3.63-3.75 (m, 2H), 7.84 (d, J=8.3 Hz, 1H), 7.94 (s, 1H), 8.03 (d, J=8.3 Hz, 1H), 9.18 (br. s., 2H).

Example 1

3-[(4-{[4-(Trifluoromethyl)phenyl]sulfonyl}-1-piperazinyl)carbonyl]pyrazolo[1,5-a]pyrimidine

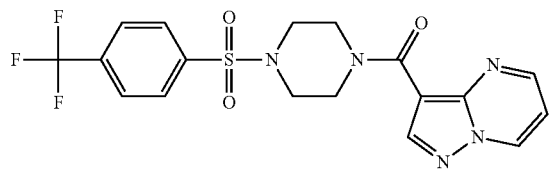

To a solution of 1-{[4-(trifluoromethyl)phenyl]sulfonyl}piperazine (may be prepared as described in Description 1) (200 mg, 0.680 mmol) in DMF (5 ml) was added pyrazolo[1,5-a]pyrimidine-3-carboxylic acid (111 mg, 0.680 mmol), HOBT.H$_2$O (104 mg, 0.680 mmol) and HBTU (258 mg, 0.680 mmol). Finally DIPEA (0.356 ml, 2.039 mmol) was added and the reaction mixture was stirred at rt for 20 hours. Solvent was removed by evaporation, the crude partitioned between DCM (50 ml) and saturated aq. sodium bicarbonate (50 ml), the DCM layer collected, dried (hydrophobic frit) and evaporated. MDAP purification yielded the title compound (317 mg) as an off-white solid.

m/z (API-ES) 440 [M+H]$^+$

1H NMR (400 MHz, CHLOROFORM-d) δ ppm 3.09-3.20 (m, 4H) 3.70-3.89 (m, 4H) 6.94 (dd, J=7.0, 4.0 Hz, 1H) 7.80 (d, J=8.5 Hz, 2H) 7.87 (d, J=8.5 Hz, 2H) 8.34 (s, 1H) 8.55 (dd, J=4.0, 2.0 Hz, 1H) 8.70 (dd, J=7.0, 2.0 Hz, 1H).

Example 2

3-[((2S)-2-Methyl-4-{[4-(trifluoromethyl)phenyl]sulfonyl}-1-piperazinyl)carbonyl]pyrazolo[1,5-a]pyrimidine

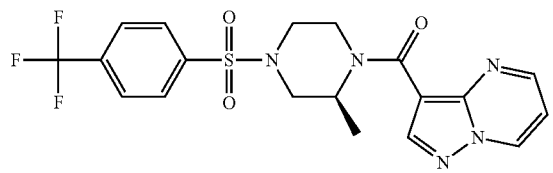

To a solution of (3S)-3-methyl-1-{[4-(trifluoromethyl)phenyl]sulfonyl}piperazine (may be prepared as described in Description 2) (80.0 mg, 0.259 mmol) in DMF (5 ml) was added pyrazolo[1,5-a]pyrimidine-3-carboxylic acid (42.3 mg, 0.259 mmol), HOBT.H$_2$O (39.7 mg, 0.259 mmol) and HBTU (98.0 mg, 0.259 mmol). Finally DIPEA (0.136 ml, 0.778 mmol) was added and the reaction mixture was stirred at room temperature for 3 hours. DMF was evaporated in vacuo then 5 ml of DCM added and washed with saturated aq. NaHCO$_3$ solution (5 ml), dried on a phase separation cartridge and evaporated in vacuo. The crude material was dissolved in MeCN/DMSO 1:1 and purified by MDAP. The desired fractions were collected and concentrated in vacuo to give the title compound as a white solid (105 mg).

m/z (API-ES) 454 [M+H]$^+$

1H NMR (400 MHz, CHLOROFORM-d) δ ppm 1.48 (d, J=6.8 Hz, 3H), 2.55 (td, J=11.8, 3.1 Hz, 1H), 2.68 (dd, J=11.6, 3.6 Hz, 1H), 3.41-3.57 (m, 1H), 3.64 (d, J=11.5 Hz, 1H), 3.81 (d, J=12.1 Hz, 1H), 4.04-4.42 (m, 1H), 4.63-4.96 (m, 1H), 6.96 (dd, J=7.0, 4.1 Hz, 1H), 7.84 (d, J=8.3 Hz, 2H), 7.90 (d, J=8.3 Hz, 2H), 8.38 (s, 1H), 8.58 (dd, J=4.1, 1.8 Hz, 1H), 8.73 (dd, J=7.0, 1.8 Hz, 1H).

Alternative Preparation of 3-[((2S)-2-Methyl-4-{[4-(trifluoromethyl)phenyl]sulfonyl}-1-piperazinyl)carbonyl]pyrazolo[1,5-a]pyrimidine Example 2a Pyrazolo[1,5-a]pyrimidine-3-carboxylic acid (11.73 g, 71.9 mmol) was suspended in thionyl chloride (36 mL, 493 mmol) and heated at 60° C. for 2 h. Formation of the acyl chloride was monitored as follows: a sample of the reaction mixture was evaporated and added to MeOH and formation of the corresponding methyl ester was detected by UPLC. Then thionyl chloride was removed under reduced pressure to obtain pyrazolo[1,5-a]pyrimidine-3-carbonyl chloride (14 g) as a yellow solid.

(2S)-2-methylpiperazine (6 g, 59.9 mmol) was dissolved in tetrahydrofuran (50 mL) and cooled down to 0° C., aqueous sodium hydroxide (3M, 39.9 mL, 120 mmol) was added and stirred for 10 min. Then 4-(trifluoromethyl)benzenesulfonyl chloride (16.12 g, 65.9 mmol) (dissolved in 50 ml of THF) was added drop-wise, stirring the reaction mixture for 1 h. THF was removed under reduced pressure, the aqueous phase was diluted with water (200 ml) and extracted with DCM (2×300 ml). The organic layer was concentrated under reduced pressure and the oily residue was suspended with HCl 1M (200 ml) and washed with DCM in order to extract impurities. NaOH 3M was added to the aqueous layer to reach pH 10 then the mixture was diluted with THF (200 ml), the mixture was cooled down to 0° C.

The pyrazolo[1,5-a]pyrimidine-3-carbonyl chloride (14 g) was suspended in THF (~80 ml) and added portion-wise to the above mixture, maintaining the pH>9 by adding NaOH 3M, and then the mixture was stirred overnight. THF was removed from the mixture under reduced pressure and the resulting suspension was extracted with DCM (2×300 ml). The organic layer was washed with HCl 0.1 M, dried over Na$_2$SO$_4$ and concentrated to dryness to obtain the crude material (21.7 g) as foam. The crude material was re-dissolved in DCM (100 ml) and evaporated to minimum volume to obtain an oily residue, ethyl ether was added (80 ml) with stirring. A solid crashed out from the solution and was recovered by filtration, washing with ethyl ether before drying to give the title compound (20.06 g).

m/z (API-ES) 454 [M+H]$^+$

1H NMR (400 MHz, CDCl$_3$) δ ppm 1.48 (d, J=7.2 Hz, 3H), 2.56 (td, J=11.6, 3.2 Hz, 1H), 2.69 (dd, J=11.6, 3.6 Hz, 1H), 3.50 (m, 1H), 3.64 (d, J=11.6 Hz, 1H), 3.82 (d, J=11.2 Hz, 1H), 4.25 (m, 1H), 4.78 (m, 1H), 6.97 (dd, J=7.2, 4.0 Hz, 1H), 7.85 (d, J=8.4 Hz, 2H), 7.91 (d, J=8.4 Hz, 2H), 8.39 (s, 1H), 8.59 (dd, J=4.0, 1.6 Hz, 1H), 8.73 (dd, J=7.2, 1.6 Hz, 1H).

Example 3

3-[((3R)-3-Methyl-4-{[4-(trifluoromethyl)phenyl]sulfonyl}-1-piperazinyl)carbonyl]pyrazolo[1,5-a]pyrimidine

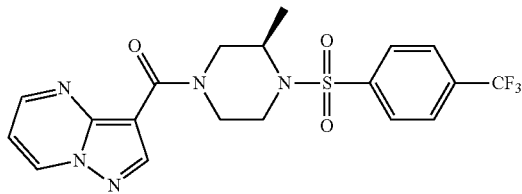

To a solution of pyrazolo[1,5-a]pyrimidine-3-carboxylic acid (56.8 mg, 0.348 mmol) in DCM (2.0 ml) was added HATU (132 mg, 0.348 mmol) and DIPEA (0.152 ml, 0.870 mmol) and the mixture stirred for 15 minutes before addition of (2R)-2-methyl-1-{[4-(trifluoromethyl)phenyl]sulfonyl}piperazine hydrochloride (may be prepared as described in Description 4) (100 mg, 0.290 mmol) in DMF (2 ml). The resultant mixture was stirred for 72 hours at rt. Water (20 ml) and EtOAc (20 ml) were added and the mixture was filtered through a sinter to remove precipitate. The collected filtrate was separated and the aqueous layer was then re-extracted with EtOAc (15 ml), the organic layers were combined and washed with saturated brine solution (20 ml). The organic layers were then separated, dried (MgSO$_4$) and concentrated to dryness. The crude material was then dissolved in DMSO and purified by MDAP. The collected fractions were concentrated in vacuo to give the title compound (85.8 mg) as a white solid.

MS ES+ m/z 454 (M+H)$^+$

1H NMR (400 MHz, CHLOROFORM-d) rotameric mixture δ ppm 1.13 (br. s., 3H), 2.73-3.84 (m, 4H), 3.86-5.00 (m, 3H), 6.97 (dd, J=7.0, 4.1 Hz, 1H), 7.80 (d, J=8.2 Hz, 2H), 7.97 (d, J=8.1 Hz, 2H), 8.41 (s, 1H), 8.61 (dd, J=4.1, 1.81 Hz, 1H), 8.74 (dd, J=7.0, 1.8 Hz, 1H).

Example 4

3-[((3S)-3-Methyl-4-{[4-(trifluoromethyl)phenyl]sulfonyl}-1-piperazinyl)carbonyl]pyrazolo[1,5-a]pyrimidine

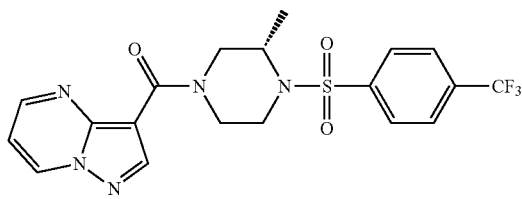

To a solution of (2S)-2-methyl-1-{[4-(trifluoromethyl)phenyl]sulfonyl}piperazine hydrochloride (may be prepared as described in Description 6) (100 mg, 0.270 mmol) in THF (5 ml) was added HOBT.H$_2$O (41.3 mg, 0.270 mmol), HBTU (102 mg, 0.270 mmol) and pyrazolo[1,5-a]pyrimidine-3-carboxylic acid (48.4 mg, 0.297 mmol). The mixture was stirred for 5 minutes before addition of DIPEA (0.118 ml, 0.674 mmol) and the resultant solution stirred at rt for 16 hours. The mixture was then concentrated and the residue partitioned between DCM (10 ml) and water (10 ml), the layers were separated using a hydrophobic frit and the organic layers concentrated to dryness and the crude material dissolved in DMSO and purified by MDAP to give the title compound (85.3 mg) as a white solid.

MS ES+ m/z 454 (M+H)$^+$

1H NMR (400 MHz, CHLOROFORM-d) rotamic mixture δ ppm 0.86-1.28 (m, 3H), 3.49 (s, 3H), 3.63-3.84 (m, 1H), 3.86-4.94 (m, 3H), 6.97 (dd, J=7.0, 4.1 Hz, 1H), 7.80 (d, J=8.3 Hz, 2H), 7.97 (d, J=8.2 Hz, 2H), 8.41 (s, 1H), 8.61 (dd, J=4.1, 1.8 Hz, 1H), 8.73 (dd, J=7.0, 1.8 Hz, 1H).

Example 5

3-Methyl-4-{[(3S)-3-methyl-4-(pyrazolo[1,5-a]pyrimidin-3-ylcarbonyl)-1-piperazinyl]sulfonyl}benzonitrile

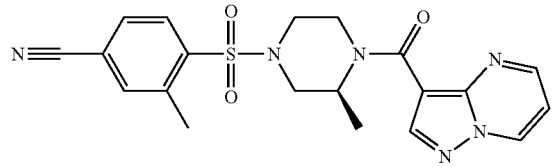

To a solution of 3-methyl-4-{[(3S)-3-methyl-1-piperazinyl]sulfonyl}benzonitrile (may be prepared as described in Description 9) (75 mg, 0.268 mmol), pyrazolo[1,5-a]pyrimidine-3-carboxylic acid (48.2 mg, 0.295 mmol) and DIPEA (0.070 ml, 0.403 mmol) in dry DMF (3 ml) at rt under argon was added HATU (122 mg, 0.322 mmol) and the resulting yellow solution stirred at rt for 1 hour. Concentration in vacuo gave a yellow oil, that was purified by MDAP; concentration of the desired fractions gave a clear film (80.2 mg). Flash chromatography (silica; Flash 12S; linear gradient (1-8%) [2M NH$_3$ in MeOH] in DCM) gave the title compound as a clear film (44.9 mg), that became a white solid on standing in vacuo (1 mbar) for 1 h.

m/z (API-ES) 425 [M+H]$^+$

1H NMR (400 MHz, CHLOROFORM-d) δ ppm 1.38 (d, J=6.9 Hz, 3H), 2.70 (s, 3H), 2.95 (td, J=11.9, 2.4 Hz, 1H), 3.11 (dd, J=12.1, 3.5 Hz, 1H), 3.37-3.50 (m, 1H), 3.60 (d, J=12.1 Hz, 1H), 3.74 (d, J=11.9 Hz, 1H), 4.23 (br. s., 1H), 4.77 (br. s., 1H), 6.97 (dd, J=7.0, 4.1 Hz, 1H), 7.61-7.67 (m, 2H), 7.98 (d, J=8.7 Hz, 1H), 8.41 (s, 1H), 8.60 (dd, J=4.1, 1.8 Hz, 1H), 8.73 (dd, J=7.0, 1.8 Hz, 1H).

Example 6

6-Methyl-3-[(4-{[4-(trifluoromethyl)phenyl]sulfonyl}-1-piperazinyl)carbonyl]pyrazolo[1,5-a]pyrimidine

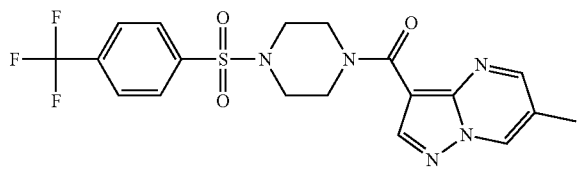

To a solution of 1-{[4-(trifluoromethyl)phenyl]sulfonyl}piperazine (may be prepared as described in Description 1) (100 mg, 0.340 mmol) in DMF (5 ml) was added HOBT.H$_2$O (52.0 mg, 0.340 mmol), HBTU (129 mg, 0.340 mmol), 6-methylpyrazolo[1,5-a]pyrimidine-3-carboxylic acid (60.2 mg, 0.340 mmol) and DIPEA (0.178 ml, 1.019 mmol), in a 2.0-5.0 ml microwave vial. The reaction mixture was stirred for 3 hours at rt. The reaction mixture was transferred to a 100 ml round bottom flask and was reduced to dryness in vacuo. The residue was dissolved in DCM (50 ml) and was transferred to a separating funnel then washed with saturated aq. NaHCO$_3$ solution (5 ml), twice. The organic layer was collected and dried with dried magnesium sulfate. The solid was removed by filtration and the filtrate collected in a 250 ml round bottom flask and reduced to dryness in vacuo. The residue was then dissolved in 1.8 ml (1:1) MeCN/DMSO and purified by MDAP in 2 batches. The fractions containing desired product were combined in a 250 ml round bottom flask and reduced in vacuo to yield the title compound (79 mg).

m/z (API-ES) 454 [M+H]$^+$

1H NMR (400 MHz, CHLOROFORM-d) δ ppm 2.43 (d, J=0.9 Hz, 3H), 3.04-3.29 (m, 4H), 3.80-3.90 (m, 4H), 7.78-7.98 (m, 4H), 8.32 (s, 1H), 8.40-8.58 (m, 2H).

Example 7

3-[((2R)-2-Methyl-4-{[4-(trifluoromethyl)phenyl]sulfonyl}-1-piperazinyl)carbonyl]pyrazolo[1,5-a]pyrimidine

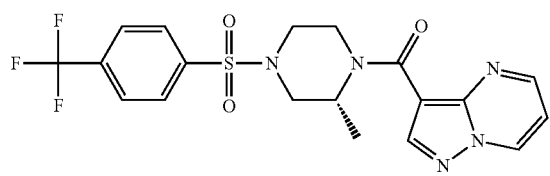

To a solution of (3R)-3-methyl-1-{[4-(trifluoromethyl)phenyl]sulfonyl}piperazine (may be prepared as described in Description 10) (80.0 mg, 0.259 mmol) in DMF (4 ml) was added pyrazolo[1,5-a]pyrimidine-3-carboxylic acid (42.3 mg, 0.259 mmol), HOBT.H$_2$O (39.7 mg, 0.259 mmol), HBTU (98 mg, 0.259 mmol) and DIPEA (0.136 ml, 0.778 mmol) and the reaction mixture was stirred at rt for 1.5 hours. The DMF was evaporated in vacuo then DCM (5 ml) was added and the whole washed with saturated aq. NaHCO$_3$ solution (5 ml), dried on a phase separation cartridge and evaporated in vacuo. The crude material was dissolved in MeCN/DMSO 1:1 and purified by MDAP to give the title compound (100 mg).

m/z (API-ES) 454 [M+H]$^+$

1H NMR (400 MHz, CHLOROFORM-d) δ ppm 1.47 (d, J=6.8 Hz, 3H), 2.55 (td, J=11.7, 3.2 Hz, 1H), 2.68 (dd, J=11.5, 3.6 Hz, 1H), 3.40-3.57 (m, 1H), 3.63 (d, J=11.4 Hz, 1H), 3.81 (d, J=10.7 Hz, 1H), 4.10-4.39 (m, 1H), 4.62-4.95 (m, 1H) 6.96 (dd, J=7.0, 4.1 Hz, 1H), 7.84 (d, J=8.3 Hz, 2H), 7.90 (d, J=8.3 Hz, 2H), 8.38 (s, 1H), 8.58 (dd, J=4.1, 1.8 Hz, 1H), 8.73 (dd, J=7.0, 1.8 Hz, 1H).

Example 8

3-{[4-({4-[(trifluoromethyl)oxy]phenyl}sulfonyl)-1-piperazinyl]carbonyl}pyrazolo[1,5-a]pyrimidine

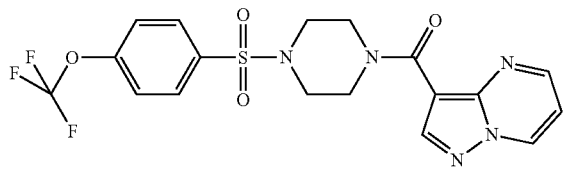

To a solution of 1-({4-[(trifluoromethyl)oxy]phenyl}sulfonyl)piperazine (may be prepared as described in Description 11) (300 mg, 0.967 mmol) in DMF (15 ml) was added pyrazolo[1,5-a]pyrimidine-3-carboxylic acid (158 mg, 0.967 mmol), HOBT.H$_2$O (148 mg, 0.967 mmol) and HBTU (368 mg, 0.967 mmol). Finally DIPEA (0.507 ml, 2.90 mmol) was added and the reaction mixture was stirred at rt for 20 hours. Solvent was removed by evaporation, the crude material partitioned between DCM (50 ml) and saturated sodium bicarbonate (50 ml), the DCM layer collected, washed with 2N HCl aq. (50 ml), dried (hydrophobic frit) and evaporated. The crude was purified by MDAP. MDAP fractions were evaporated and the crude material partitioned between DCM (20 ml) and sat. sodium bicarbonate solution (20 ml). The DCM layer was collected and dried (hydrophobic frit) and evaporated to give the title compound (308 mg).

m/z (API-ES) 456 [M+H]$^+$

1H NMR (400 MHz, CHLOROFORM-d) δ ppm 3.16 (d, 4H), 3.84 (br. s., 4H), 6.96 (dd, J=7.0, 4.1 Hz, 1H), 7.32-7.45 (m, 2H), 7.76-7.88 (m, 2H), 8.38 (s, 1H), 8.58 (dd, J=4.1, 1.8 Hz, 1H), 8.72 (dd, J=7.0, 1.8 Hz, 1H).

Example 9

6-Fluoro-3-[((2S)-2-methyl-4-{[4-(trifluoromethyl)phenyl]sulfonyl}-1-piperazinyl)carbonyl]pyrazolo[1,5-a]pyrimidine

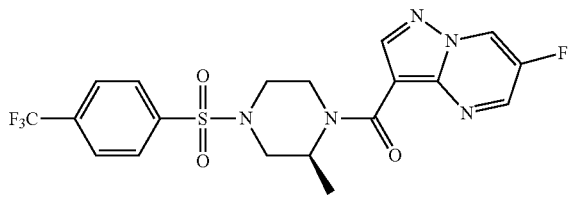

The lithium salt of 6-fluoropyrazolo[1,5-a]pyrimidine-3-carboxylate (117 mg, 0.63 mmol) (may be prepared as described in Description 16) was weighed into a vial with HATU (247 mg, 0.65 mmol), suspended in DMF (2 ml) and treated with DIPEA (0.170 ml, 0.97 mmol). This mixture was stirred about 15 min at ambient temperature. (3S)-3-Methyl-1-{[4-(trifluoromethyl)phenyl]sulfonyl}piperazine (may be prepared as described in Description 2) (100 mg, 0.32 mmol) was added and stirring was continued for 3 h at ambient temperature. The reaction mixture was partitioned between DCM and sat. aq. NaHCO$_3$ solution (10 ml each). The layers were separated (hydrophobic frit) and the aqueous layer was washed with further DCM (2×5 ml). The combined organic layers were concentrated to leave an orange gum. Purification by MDAP gave the title compound (112 mg, 0.24 mmol, 73% yield) as an orange solid.

m/z (API-ES) 472 [M+H]$^+$

1H NMR (400 MHz, DMSO-d$_6$) δ ppm 1.28 (d, J=6 Hz, 3H), 2.38-2.48 (m, 1H), 2.54 (dd, J=11, 3 Hz, 1H), 3.28-3.40 (m, 1H, obscured by water), 3.47-3.55 (m, 1H), 3.64-3.73 (m, 1H), 3.90-4.15 (m, 1H), 4.40-4.70 (m, 1H), 7.97 (d, J=8 Hz, 2H), 8.06 (d, J=8 Hz, 2H), 8.40 (s, 1H), 8.90 (d, J=3 Hz, 1H), 9.64 (dd, J=5, 3 Hz, 1H).

Example 10

4-({(3S)-4-[(6-fluoropyrazolo[1,5-a]pyrimidin-3-yl)carbonyl]-3-methyl-1-piperazinyl}sulfonyl)-3-methylbenzonitrile

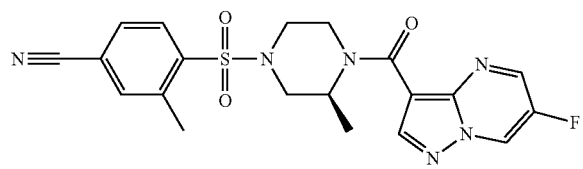

To a solution of 3-methyl-4-{[(3S)-3-methyl-1-piperazinyl]sulfonyl}benzonitrile (may be prepared as described in Description 9) (100 mg, 0.317 mmol), lithium 6-fluoropyrazolo[1,5-a]pyrimidine-3-carboxylate (may be prepared as described in Description 16) (65.5 mg, 0.348 mmol), HOBT (58.2 mg, 0.380 mmol) and Et$_3$N (0.110 ml, 0.792 mmol) in dry DMF (50 ml) at rt under Ar was added HBTU (144 mg, 0.380 mmol) and the resulting dark brown solution stirred at rt for 16 h. The mixture was concentrated under vacuum to leave a black oil. Purification by MDAP and concentration of the desired fractions gave a yellow film (109 mg). Flash chromatography (silica; Flash 12M; 3:1, EtOAc:isohexane) gave the title compound as a white foam (57.1 mg), that became a white solid on trituration with ether.

m/z (API-ES) 443 [M+H]$^+$ $^1$H NMR (400 MHz, CHLOROFORM-d) δ ppm 1.38 (d, J=6.9 Hz, 3H), 2.69 (s, 3H), 2.91 (td, J=12.1, 3.1 Hz, 1H), 3.08 (dd, J=12.2, 3.6 Hz, 1H), 3.35-3.52 (m, 1H), 3.60 (d, J=12.2 Hz, 1H), 3.74 (d, J=12.1 Hz, 1H), 4.12 (br. s., 1H), 4.72 (br. s., 1H), 7.61-7.67 (m, 2H), 7.98 (d, J=8.7 Hz, 1H), 8.40 (s, 1H), 8.65 (d, J=2.6 Hz, 1H), 8.69 (dd, J=3.5, 2.7 Hz, 1H)

Example 11

3-{[(2S)-2-methyl-4-({4-[(trifluoromethyl)oxy]phenyl}sulfonyl)-1-piperazinyl]carbonyl}pyrazolo[1,5-a]pyrimidine

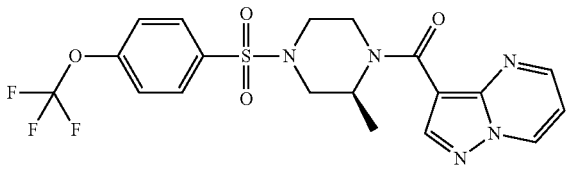

To a solution of (3S)-3-methyl-1-({4-[(trifluoromethyl)oxy]phenyl}sulfonyl)piperazine (may be prepared as described in Description 13) (300 mg, 0.925 mmol), HOBt (142 mg, 0.925 mmol), HBTU (351 mg, 0.925 mmol) and pyrazolo[1,5-a]pyrimidine-3-carboxylic acid (151 mg, 0.925 mmol) in DMF (50 ml) was added DIPEA (0.485 ml, 2.78 mmol) and the resulting mixture stirred at room temperature overnight, then concentrated under vacuum. The residue was redissolved in EtOAc, washed with aqueous NaHCO$_3$ and brine, then concentrated under vacuum. Flash chromatography (silica; EtOAc) and concentration of the desired fractions gave the title compound (157 mg).

m/z (API-ES) 470 [M+H]$^+$ $^1$H NMR (400 MHz, CHLOROFORM-d) δ ppm 1.45 (d, J=6.8 Hz, 3H), 2.53 (td, J=11.7, 3.3 Hz, 1H), 2.66 (dd, J=11.5, 3.6 Hz, 1H), 3.36-3.54 (m, 1H), 3.60 (d, J=11.3 Hz, 1H), 3.77 (d, J=10.9 Hz, 1H), 4.30 (br. s., 1H), 4.76 (br. s., 1H), 6.95 (dd, J=7.0, 4.1 Hz, 1H), 7.37 (dd, J=8.9, 0.9 Hz, 2H), 7.77-7.84 (m, 2H), 8.35 (s, 1H), 8.57 (dd, J=4.1, 1.8 Hz, 1H), 8.72 (dd, J=7.0, 1.8 Hz, 1H)

Example 12

6-bromo-3-[((2S)-2-methyl-4-{[4-(trifluoromethyl)phenyl]sulfonyl}-1-piperazinyl)carbonyl]pyrazolo[1,5-a]pyrimidine

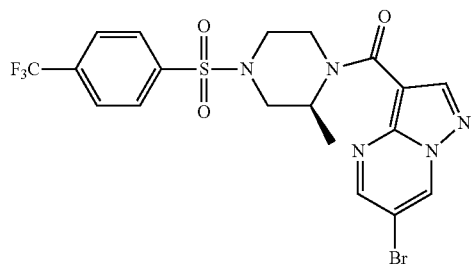

To a solution of 6-bromopyrazolo[1,5-a]pyrimidine-3-carboxylic acid (may be prepared as described in Description 17) (471 mg, 1.946 mmol) in N,N-Dimethylformamide (10 mL) under a flush of argon was added HATU (740 mg, 1.946 mmol) and the reaction stirred for 10 minutes. (3S)-3-methyl-1-{[4-(trifluoromethyl)phenyl]sulfonyl}piperazine (may be prepared as described in Description 2) (600 mg, 1.946 mmol) was then added followed by N,N-diisopropylethylamine (0.680 mL, 3.89 mmol) and the reaction stirred for 18 h. The reaction mixture was partitioned between ethyl acetate (60 mL) and water (40 mL). The organic layer was washed with further water (20 mL) and brine (20 mL) before it was dried (MgSO$_4$), filtered and the solvent removed in vacuo. The crude material was purified by silica chromatography, 40 M cartridge, eluting 0-75% EtOAC in isohexane and the solvent evaporated to give the title compound (587 mg) as a white solid.

m/z (API-ES) 532+534 (1:1) [M+H]$^+$

1H NMR (400 MHz, DMSO-d$_6$) δ ppm 1.28 (d, J=7.2 Hz, 3H), 2.35-2.55 (m, 3H), 3.51 (m, 1H), 3.68 (m, 1H), 4.02 (m, 1H), 4.57 (m, 1H), 7.97 (d, J=8.4 Hz, 2H), 8.06 (d, J=8.4 Hz, 2H), 8.37 (s, 1H), 8.73 (d, J=2.4 Hz, 1H), 9.69 (d, J=2.4 Hz, 1H).

Example 13

3-[((2S)-2-methyl-4-{[4-(trifluoromethyl)phenyl]sulfonyl}-1-piperazinyl)carbonyl]pyrazolo[1,5-a]pyrimidine-6-carbonitrile

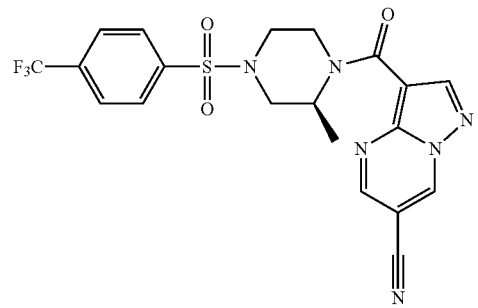

To a mixture of 6-bromo-3-[((2S)-2-methyl-4-{[4-(trifluoromethyl)phenyl]sulfonyl}-1-piperazinyl)carbonyl]pyrazolo[1,5-a]pyrimidine (may be prepared as described in Example 12) (300 mg, 0.564 mmol) and 1,1'-bis(diphenylphosphino)ferrocene (39.1 mg, 0.070 mmol) under argon in dry N,N-dimethylformamide (6 mL) was added zinc cyanide (86 mg, 0.733 mmol) followed by tris(dibenzylideneacetone)dipalladium(0) (32.0 mg, 0.035 mmol) and the mixture heated to 95° C. for 2 h. The mixture was partitioned between ethyl acetate (30 mL) and aqueous sodium bicarbonate (20 mL). The organic phase was washed with further sodium bicarbonate (10 mL), water (10 mL) and brine (10 mL) before it was dried (MgSO$_4$), filtered and the solvent removed in vacuo. Half the crude material was purified by MDAP and the solvent evaporated to give the title compound (67 mg) as a yellow solid.

m/z (API-ES) 479 [M+H]$^+$

1H NMR (400 MHz, DMSO-d$_6$) δ ppm 1.28 (d, J=6.8 Hz, 3H), 2.4-2.6 and 3.4-4.7 (m, 5H), 7.97 (d, J=8.0 Hz, 2H), 8.06 (d, J=8.0 Hz, 2H), 8.59 (s, 1H), 8.91 (d, J=2.0 Hz, 1H), 10.07 (d, J=2.0 Hz, 1H).

Examples 14 to 24

The compounds of Table 1 were prepared in a similar manner as the compound of Example 1 using the corresponding reactants.

TABLE 1

| Example no. | Name | Structure | m/z (API-ES) [M + H]$^+$ |
|---|---|---|---|
| 14 | 5,7-dimethyl-3-[(4-{[4-(trifluoromethyl)phenyl]sulfonyl}-1-piperazinyl)carbonyl]pyrazolo[1,5-a]pyrimidine | 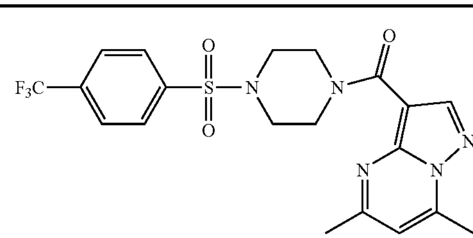 | 468 |

TABLE 1-continued

| Example no. | Name | Structure | m/z (API-ES) [M + H]+ |
|---|---|---|---|
| 15 | 3-{[(3S)-3-methyl-4-({4-[(trifluoromethyl)oxy]phenyl}sulfonyl)-1-piperazinyl]carbonyl}pyrazolo[1,5-a]pyrimidine | 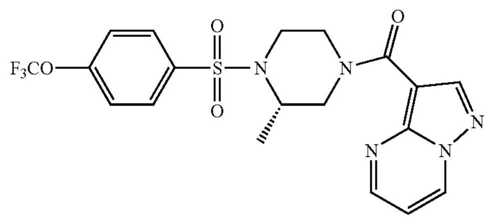 | 470 |
| 16 | 4-({(3S)-4-[(6-chloropyrazolo[1,5-a]pyrimidin-3-yl)carbonyl]-3-methyl-1-piperazinyl}sulfonyl)-3-methylbenzonitrile | 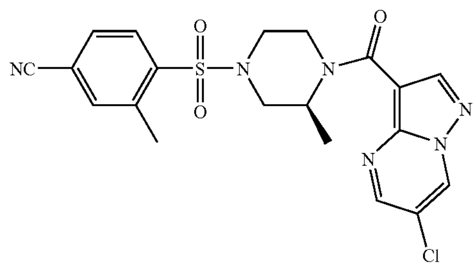 | 459 + 461 (3:1) |
| 17 | 6-chloro-3-[((2S)-2-methyl-4-{[4-(trifluoromethyl)phenyl]sulfonyl}-1-piperazinyl)carbonyl]pyrazolo[1,5-a]pyrimidine | 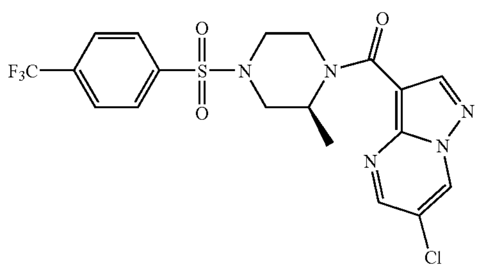 | 488 + 490 (3:1) |
| 18 | 3-[((2S)-2-methyl-4-{[2-methyl-5-(trifluoromethyl)phenyl]sulfonyl}-1-piperazinyl)carbonyl]pyrazolo[1,5-a]pyrimidine | 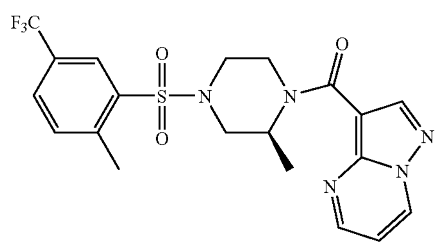 | 468 |
| 19 | 3-[(4-{[2-methyl-5-(trifluoromethyl)phenyl]sulfonyl}-1-piperazinyl)carbonyl]pyrazolo[1,5-a]pyrimidine | 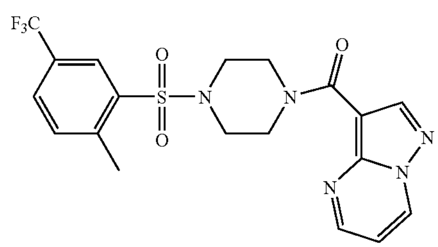 | 454 |
| 20 | 2-methyl-3-[((2S)-2-methyl-4-{[4-(trifluoromethyl)phenyl]sulfonyl}-1-piperazinyl)carbonyl]pyrazolo[1,5-a]pyrimidine | 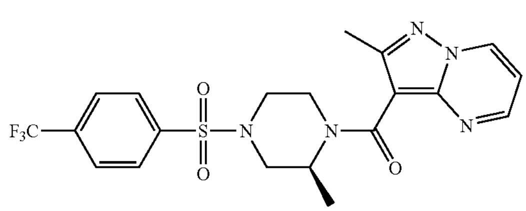 | 468 |

TABLE 1-continued

| Example no. | Name | Structure | m/z (API-ES) [M + H]+ |
|---|---|---|---|
| 21 | 3-{[(3R)-3-methyl-4-({4-[(trifluoromethyl)oxy]phenyl}sulfonyl)-1-piperazinyl]carbonyl}pyrazolo[1,5-a]pyrimidine | 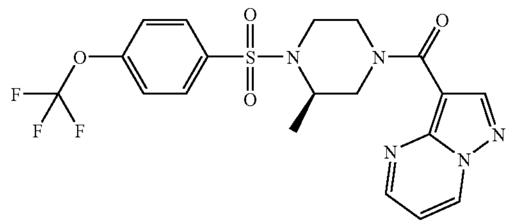 | 470 |
| 22 | 3-{[(2R)-2-methyl-4-({4-[(trifluoromethyl)oxy]phenyl}sulfonyl)-1-piperazinyl]carbonyl}pyrazolo[1,5-a]pyrimidine | 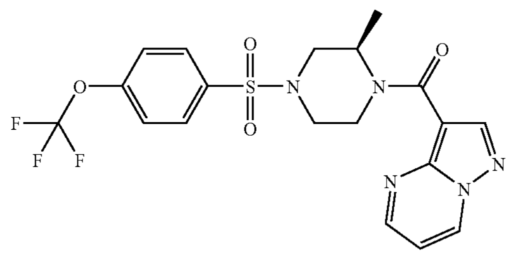 | 470 |
| 23 | 3-methyl-4-({(3S)-3-methyl-4-[(6-methylpyrazolo[1,5-a]pyrimidin-3-yl)carbonyl]-1-piperazinyl}sulfonyl)benzonitrile | 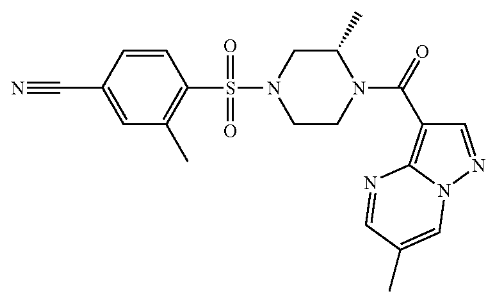 | 439 |
| 24 | 3-methyl-4-({(3S)-3-methyl-4-[(2-methylpyrazolo[1,5-a]pyrimidin-3-yl)carbonyl]-1-piperazinyl}sulfonyl)benzonitrile | 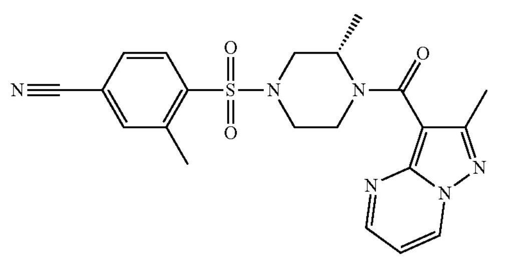 | 439 |

Example 25

3-[((2S)-2-methyl-4-{[2-methyl-4-(trifluoromethyl)phenyl]sulfonyl}-1-piperazinyl)carbonyl]pyrazolo[1,5-a]pyrimidine

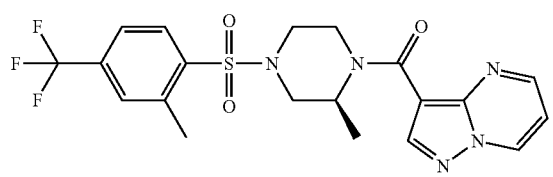

To a solution of (3S)-3-methyl-1-{[2-methyl-4-(trifluoromethyl)phenyl]sulfonyl}piperazine (100 mg, 0.310 mmol) (may be prepared as described in Description 27), pyrazolo[1,5-a]pyrimidine-3-carboxylic acid (55.7 mg, 0.341 mmol), HOBt (52.3 mg, 0.341 mmol) and DIPEA (0.081 ml, 0.465 mmol) in dry DMF (5 ml) at rt was added HBTU (129 mg, 0.341 mmol) and the resulting orange solution stirred at rt for 45 min. Concentration under vacuum left an orange oil. Purification by MDAP and concentration of the desired fractions gave the title compound (108 mg) as a clear film that became a white solid on trituration with ether.

m/z (API-ES) 468 [M+H]+

1H NMR (400 MHz, CHLOROFORM-d) δ ppm 1.39 (d, J=6.9 Hz, 3H), 2.73 (s, 3H), 2.94 (td, J=11.9, 2.7 Hz, 1H), 3.10 (dd, J=12.1, 3.6 Hz, 1H), 3.36-3.54 (m, 1H), 3.61 (d, J=12.1 Hz, 1H), 3.75 (d, J=12.0 Hz, 1H), 4.22 (br. s., 1H), 4.77 (br. s., 1H), 6.97 (dd, J=7.0, 4.1 Hz, 1H), 7.57-7.66 (m, 2H), 7.96-8.06 (m, 1H), 8.42 (s, 1H), 8.61 (dd, J=4.1, 1.8 Hz, 1H), 8.74 (dd, J=7.0, 1.8 Hz, 1H)

Equipment:

Mass-Directed Automated HPLC/Mass-Directed Automated Preparation (MDAP)

Where indicated in the above Examples, purification by mass-directed automated HPLC was carried out using the following apparatus and conditions:

Hardware
Waters 2525 Binary Gradient Module
Waters 515 Makeup Pump
Waters Pump Control Module
Waters 2767 Inject Collect
Waters Column Fluidics Manager
Waters 2996 Photodiode Array Detector
Waters ZQ Mass Spectrometer
Gilson 202 fraction collector
Gilson Aspec waste collector
Software
Waters MassLynx version 4 SP2
Column The columns used are Waters Atlantis, the dimensions of which are 19 mm×100 mm (small scale) and 30 mm×100 mm (large scale). The stationary phase particle size is 5 μm.

Solvents
A: Aqueous solvent=Water+0.1% Formic Acid
B: Organic solvent=Acetonitrile+0.1% Formic Acid
Make up solvent=Methanol:Water 80:20
Needle rinse solvent=Methanol
Methods There are five methods used depending on the analytical retention time of the compound of interest. They have a 13.5-minute runtime, which comprises of a 10-minute gradient followed by a 3.5 minute column flush and re-equilibration step.

Large/Small Scale 1.0-1.5=5-30% B
Large/Small Scale 1.5-2.2=15-55% B
Large/Small Scale 2.2-2.9=30-85% B
Large/Small Scale 2.9-3.6=50-99% B
Large/Small Scale 3.6-5.0=80-99% B (in 6 minutes followed by 7.5 minutes flush and re-equilibration)

Flow Rate
All of the above methods have a flow rate of either 20 mls/min (Small Scale) or 40 mls/min (Large Scale).

Liquid Chromatography/Mass Spectrometry
Analysis of the above compounds by Liquid Chromatography/Mass Spectrometry (LC/MS) was carried out using the following apparatus and conditions:

Hardware
Waters Acquity Binary Solvent Manager
Waters Acquity Sample Manager
Waters Acquity PDA
Waters ZQ Mass Spectrometer
Sedere Sedex 75
Software
Waters MassLynx version 4.1
Column The column used is a Waters Acquity BEH UPLC C18, the dimensions of which are 2.1 mm×50 mm. The stationary phase particle size is 1.7 μm.

Solvents
A: Aqueous solvent=Water+0.05% Formic Acid
B: Organic solvent=Acetonitrile+0.05% Formic Acid
Weak Wash=1:1 Methanol:Water
Strong Wash=Water
Method The generic method used has a 2 minute runtime.

| Time/min | % B |
|---|---|
| 0 | 3 |
| 0.1 | 3 |
| 1.5 | 97 |
| 1.9 | 97 |
| 2.0 | 3 |

The above method has a flow rate of 1 ml/min.
The injection volume for the generic method is 0.5 ul
The column temperature is 40° C.
The UV detection range is from 220 to 330 nm
Biotage SP4®

Biotage-SP4® is an automated purification system. It uses preloaded silica gel columns. The user applies their material to the top of the column and chooses solvents, gradients, flow rates, column size, collection method and eluting volumes.

Phase Separators (Hydrophobic Frit)

Phase separators are a range of ISOLUTE® columns fitted with an optimized frit material that easily separates aqueous phase from chlorinated solvents under gravity.

SCX—Strong Cation Exchange Cartridge

Where indicated in the compounds, an SCX cartridge was used as part of the compound purification process. Typically an ISOLUTE SCX-2 cartridge was used. ISOLUTE SCX-2 is a silica-based sorbent with a chemically bonded propylsulfonic acid functional group.

ISOLUTE SCX-2 Chemical Data
Base Material: Silica, 50 μm
Functional Group: Propylsulfonic acid
Capacity: 0.6 meq/g
Counter Ion: Proton
Pharmacological Data Compounds of the invention may be tested for in vitro biological activity in the $hCa_V2.2$ assay in accordance with the following studies:

Methods
Cell Biology

Stable cell lines expressing the human $Ca_V2.2$ α ($α1_B$) subunit, along with the human β3 and α2δ1 auxiliary subunits were created following sequential transfection and selection of human embryonic kidney (HEK293) cells. HEK293 cells were cultured in Dulbecco's modified Eagles media/F12 media (Invitrogen, Cat #041-95750V) containing 10% fetal bovine serum, with added L-glutamine (2 mM; Invitrogen, Cat #25030-024) and non-essential amino acids (5%; Invitrogen, Cat #11140-035). Initially HEK293 cells were transfected with two plasmid vectors for expression of the $hCa_V2.2$ α subunit (pCIN5-$hCa_V2.2$ which carries a neomycin resistance marker) and the $hCa_V$ β3 subunit (pCIH-$hCa_V$ β3 which carries a hygromycin resistance marker). Clonal cell lines were isolated following selection in media supplemented with 0.4 mg ml$^{-1}$ Geneticin G418 (Invitrogen, Cat #10131-027) and 0.1 mg ml$^{-1}$ hygromycin (Invitrogen, Cat #10687-010). These clonal cell lines were assessed for $Ca_V2.2$ α/β3-mediated current expression using the IonWorks planar array electrophysiology technology (described below). A clonal line was identified that gave a reasonable level of functional $Ca_V2.2$ α/β3 current expression. This cell line was transfected with a plasmid vector for expression of the human α2δ1 subunit (pCIP-α2δ1 which carries a puromycin resistance marker) and clonal cell lines isolated following selection in media containing 0.62 μg ml$^{-1}$ puromycin (Sigma, Cat #P-7255), in addition to 0.4 mg ml$^{-1}$ Geneticin G418 and 0.1 mg ml$^{-1}$ hygromycin. Several cell lines were identified that gave robust levels of $Ca_V2.2$ α/β3/α2δ1-mediated current expression and one of these was selected for compound profiling. Expression of all three subunits within this cell line was continuously maintained by the inclusion of G418 (0.4 mg ml$^{-1}$), hygromycin (0.1 mg ml$^{-1}$) and puromycin (0.62 µg ml$^{-1}$). Cells were maintained at 37° C. in a humidified environment containing 5% $CO_2$ in air. Cells were liberated from the T175 culture flasks for passage and harvesting using TrpLE (Invitrogen, Cat #12604-013).

Cell Preparation

Cells were grown to 30-60% confluence in T175 flasks and maintained at 30° C. for 24 hours prior to recording. Cells were lifted by removing the growth media, washing with $Ca^{2+}$ free PBS (Invitrogen, Cat #14190-094) and incubating with 3 ml of warmed (37° C.) TrpLE (Invitrogen, Cat #12604-013) for 6 minutes. Lifted cells were suspended in 10 ml of extracellular buffer. Cell suspension was then placed into a 15 ml tube and centrifuged for 2 minutes at 700 rpm. After centrifugation, the supernatant was removed and the cell pellet was resuspended in 4.5 ml of extracellular solution.

Electrophysiology

Currents were recorded at room temperature (21-23° C.) using the IonWorks planar array electrophysiology technology (Molecular Devices Corp.). Stimulation protocols and data acquisition were carried out using a microcomputer (Dell Pentium 4). In order to determine planar electrode hole resistances (Rp), a 10 mV, 160 ms potential difference was applied across each hole. These measurements were performed before cell addition. After cell addition a seal test was performed prior to antibiotic (amphotericin) circulation to achieve intracellular access. Leak subtraction was conducted in all experiments by applying a 160 ms hyperpolarizing (10 mV) prepulse 200 ms before the test pulses to measure leak conductance. Test pulses stepping from the holding potential ($V_H$) of −90 mV to +10 mV were applied for 20 ms and repeated 10 times at a frequency of 10 Hz. In all experiments, the test pulse protocol was performed in the absence (pre-read) and presence (post-read) of a compound. Pre- and post-reads were separated by a compound addition followed by a 3-3.5 min incubation.

Solutions and Drugs

The intracellular solution contained the following (in mM): K-gluconate 120, KCl 20 mM, $MgCl_2$ 5, EGTA 5, HEPES 10, adjusted to pH 7.3. Amphotericin was prepared as 30 mg/ml stock solution and diluted to a final working concentration of 0.2 mg ml$^{-1}$ in intracellular buffer solution. The extracellular solution contained the following (in mM): Na-gluconate 120, NaCl 20, $MgCl_2$ 1, HEPES 10, $BaCl_2$ 5, adjusted to pH 7.4.

Compounds were generally prepared in DMSO as 10 mM stock solutions and subsequent 1:3 serial dilutions performed. Finally the compounds were diluted 1:100 in external solution resulting in a final DMSO concentration of 1%.

Data Analysis

The recordings were analyzed and filtered using seal resistance (>40 MΩ), resistance reduction (>35%) and peak current amplitude (>200 pA) in the absence of compound to eliminate unsuitable cells from further analysis. Paired comparisons between pre-compound and post-compound additions were used to determine the inhibitory effect of each compound. The concentrations of compounds required to inhibit current elicited by the 1$^{st}$ depolarizing pulse by 50% (tonic pIC50) were determined by fitting of the Hill equation to the concentration response data. In addition the use-dependent inhibitory properties of the compounds were determined by assessing the effect of compounds on the 10$^{th}$ versus 1$^{st}$ depolarizing pulse. The ratio of the 10$^{th}$ over 1$^{st}$ pulse was determined in the absence and presence of drug and the % use-dependent inhibition calculated. The data was fitted using the same equation as for the tonic pIC$_{50}$ and the concentration producing 30% inhibition (use-dependent pUD$_{30}$) determined.

The compounds of Examples 1 to 11, 13 to 24 were tested in the hCa$_V$2.2 assay and demonstrated the following pUD$_{30}$ and pIC$_{50}$ values. Compounds were tested in the form as described in the Examples. All compounds tested have been tested one or more times (up to 12 times). Variations in pUD$_{30}$ and pIC$_{50}$ values may arise between tests.

The compounds 1 to 11, 13, 15 to 24 exhibited a pUD$_{30}$ value of 4.5 or more than 4.5. The compounds 1 to 11, 13, 15 to 23 exhibited a pUD$_{30}$ value of 5.0 or more than 5.0. The compounds 3, 4, 9, 11, 13, 16, 17 and 18 exhibited a pUD$_{30}$ value of 5.5 or more than 5.5.

The compounds 1 to 11, 14 to 16, and 18 to 24 exhibited a mean pIC$_{50}$ value of 5.0 or less than 5.0. The compounds 1, 3 to 8, 10, 11, 14, 15, 18, 19, and 21 to 24 exhibited a mean pIC$_{50}$ value of 4.5 or less than 4.5.

The invention claimed is:

1. A compound of formula (I), or a salt thereof,

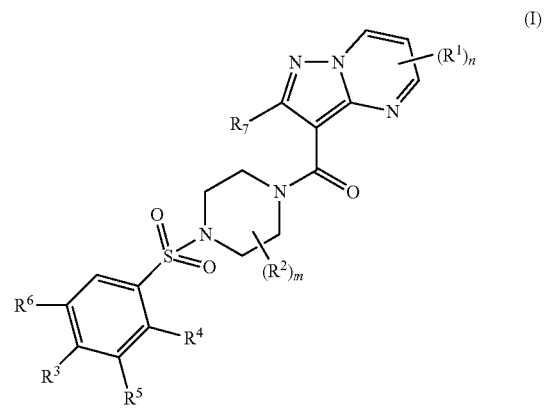

$R^1$ is $C_{1-4}$ alkyl, halogen or cyano;
m and n are selected from 0, 1 and 2;
$R^2$ is $C_{1-4}$ alkyl;
$R^3$ is hydrogen, cyano, $C_{1-4}$ haloalkyl, $C_{1-4}$ haloalkoxy or halogen;
$R^4$ is hydrogen or $C_{1-4}$ alkyl;
$R^5$ is hydrogen, cyano, $C_{1-4}$ haloalkyl, $C_{1-4}$ haloalkoxy or halogen;
$R^6$ is hydrogen, cyano, $C_{1-4}$ haloalkyl, $C_{1-4}$ haloalkoxy or halogen;
such that at least 1 of $R^3$, $R^4$, $R^5$ and $R^6$ is a group other than hydrogen;
$R^7$ is hydrogen or $C_{1-4}$ alkyl; such that when $R^7$ is $C_{1-4}$ alkyl, n is 0.

2. The compound or salt according to claim 1, wherein n is 0 or 1.

3. The compound or salt according to claim 2, wherein n is 0.

4. The compound or salt according to claim 1, wherein $R^1$ is selected from methyl, fluoro, chloro and cyano.

5. The compound or salt according to claim 4, wherein $R^1$ is selected from methyl and fluoro.

6. The compound or salt according to claim 1, wherein $R^7$ is selected from hydrogen and methyl.

7. The compound or salt according to claim 6, wherein $R^7$ is hydrogen.

8. The compound or salt according to claim 1, wherein $R^2$ is methyl.

9. The compound or salt according to claim 8, wherein $R^2$ is methyl and m is 1.

10. The compound or salt according to claim 9, wherein the compound is a compound of formula (Ib

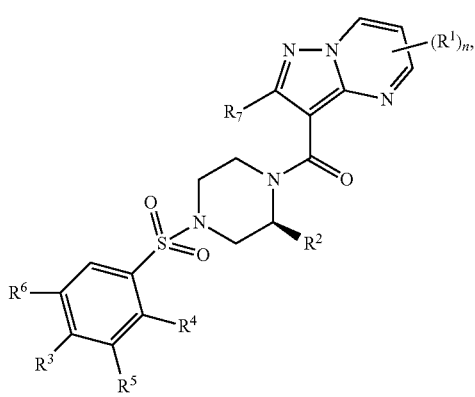

(Ib)

or a salt thereof.

11. The compound or salt according to claim 1, wherein $R^3$ is selected from trifluoromethyl, cyano, trifluoromethoxy and hydrogen.

12. The compound or salt according to claim 11, wherein $R^3$ is selected from trifluoromethyl and trifluoromethoxy.

13. The compound or salt according to claim 12, wherein $R^3$ is trifluoromethyl.

14. The compound or salt according to claim 1, wherein $R^4$ is hydrogen or methyl.

15. The compound or salt according to claim 14, wherein $R^4$ is hydrogen.

16. The compound or salt according to claim 1, wherein $R^5$ and $R^6$ are independently selected from hydrogen and $C_{1-4}$ haloalkyl.

17. The compound or salt according to claim 16, wherein $R^5$ and $R^6$ are independently selected from hydrogen and trifluoromethyl.

18. The compound or salt according to claim 17, wherein $R^5$ and $R^6$ are hydrogen.

19. The compound or salt according to claim 1, of formula

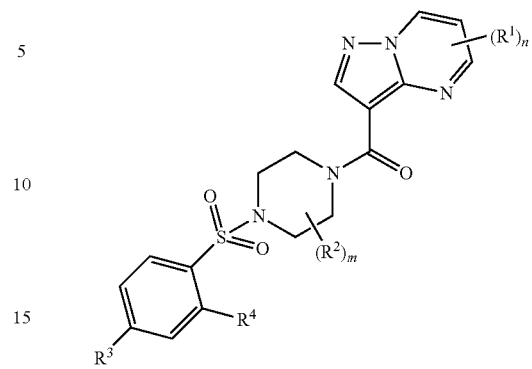

wherein $R^1$ represents $C_{1-4}$ alkyl;
n represents an integer from 0 or 1;
m represents an integer from 0 to 1;
$R^2$ represents $C_{1-4}$ alkyl;
$R^3$ represents cyano, trifluoromethyl or trifluoromethoxy;
$R^4$ represents hydrogen or methyl;
such that when $R^3$ represents cyano, $R^4$ represents a group other than hydrogen;
or a salt thereof.

20. The compound, or a pharmaceutically acceptable salt thereof, according to claim 1, which is 3-[((2S)-2-Methyl-4-{[4-(trifluoromethyl)phenyl]sulfonyl}-1-piperazinyl)carbonyl]pyrazolo[1,5-a]pyrimidine of formula

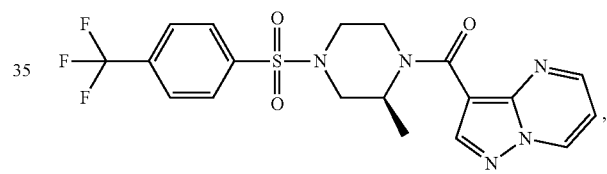

or a salt thereof.

21. The compound or salt according to claim 1, wherein the salt is a pharmaceutically acceptable salt.

22. A pharmaceutical composition comprising (a) a compound or salt according to claim 21, and (b) a pharmaceutically acceptable excipient.

23. A method for the treatment of neuropathic pain or inflammatory pain in a human in need thereof comprising administering to said human a therapeutically effective amount of a compound according to claim 21.

* * * * *